(12) United States Patent
Shah et al.

(10) Patent No.: US 8,721,722 B2
(45) Date of Patent: May 13, 2014

(54) INTERVERTEBRAL IMPLANT AND ASSOCIATED METHOD

(75) Inventors: Gretchen Dougherty Shah, Wayne, NJ (US); Hyun Bae, Santa Monica, CA (US); Ryan C. Lakin, Newton, NJ (US); Nathaniel E. Hawkins, Chatham, NJ (US)

(73) Assignee: EBI, LLC, Parsippany, NJ (US)

( * ) Notice: Subject to any disclaimer, the term of this patent is extended or adjusted under 35 U.S.C. 154(b) by 1646 days.

(21) Appl. No.: 11/567,272

(22) Filed: Dec. 6, 2006

(65) Prior Publication Data
US 2007/0118224 A1 May 24, 2007

Related U.S. Application Data

(63) Continuation-in-part of application No. 11/248,101, filed on Oct. 12, 2005, now abandoned.

(60) Provisional application No. 60/619,842, filed on Oct. 18, 2004.

(51) Int. Cl.
*A61F 2/44* (2006.01)
(52) U.S. Cl.
USPC .................................. 623/17.15; 623/17.11
(58) Field of Classification Search
USPC ............................................ 623/17.11–17.16
See application file for complete search history.

(56) References Cited

U.S. PATENT DOCUMENTS

| | | | |
|---|---|---|---|
| 3,848,601 A | 11/1974 | Ma et al. | |
| 3,875,595 A | 4/1975 | Froning | |
| 3,892,232 A | 7/1975 | Neufeld | |
| 4,272,855 A | 6/1981 | Frey | |
| 4,309,777 A | 1/1982 | Patil | |
| 4,341,206 A | 7/1982 | Perrett et al. | |
| 4,349,921 A | 9/1982 | Kuntz | |
| 4,450,834 A | 5/1984 | Fischer | |
| 4,501,269 A | 2/1985 | Bagby | |
| 4,526,909 A | 7/1985 | Urist | |
| 4,596,574 A | 6/1986 | Urist | |

(Continued)

FOREIGN PATENT DOCUMENTS

DE 2 263 842 7/1974
DE 30 23 353 4/1981

(Continued)

OTHER PUBLICATIONS

"PCT Invitation to Pay Additional Fees" with partial international search included as an annex for PCT/US2007/025020 mailed May 7, 2008.

(Continued)

*Primary Examiner* — Thomas J Sweet
*Assistant Examiner* — Christopher D Prone
(74) *Attorney, Agent, or Firm* — Harness, Dickey

(57) ABSTRACT

An intervertebral implant and associated method. The intervertebral implant can include a first component having a first articulating surface and a first bone engagement surface for engaging a first vertebra, and a second component having a second articulating surface and a second bone engagement surface for engaging a second vertebra adjacent to the first vertebra. The first and second articulating surfaces articulate with each other for substantially replicating a natural spinal movement. The first and second bone engagement surfaces define an outer surface substantially shaped as an envelope of five cylinders.

26 Claims, 28 Drawing Sheets

(56) References Cited

U.S. PATENT DOCUMENTS

| | | | |
|---|---|---|---|
| 4,599,086 | A | 7/1986 | Doty |
| 4,620,327 | A | 11/1986 | Caplan et al. |
| 4,623,553 | A | 11/1986 | Ries et al. |
| 4,714,469 | A | 12/1987 | Kenna |
| 4,743,256 | A | 5/1988 | Brantigan |
| 4,759,766 | A | 7/1988 | Buettner-Janz et al. |
| 4,772,287 | A | 9/1988 | Ray et al. |
| 4,878,915 | A | 11/1989 | Brantigan |
| 4,997,432 | A | 3/1991 | Keller |
| 5,015,247 | A | 5/1991 | Michelson |
| 5,026,373 | A | 6/1991 | Ray et al. |
| 5,147,402 | A | 9/1992 | Bohler et al. |
| 5,258,031 | A | 11/1993 | Salib et al. |
| 5,258,043 | A | 11/1993 | Stone |
| 5,282,861 | A | 2/1994 | Kaplan |
| 5,306,307 | A | 4/1994 | Senter et al. |
| 5,306,308 | A | 4/1994 | Gross et al. |
| 5,306,309 | A | 4/1994 | Wagner et al. |
| 5,308,412 | A | 5/1994 | Shetty et al. |
| 5,314,477 | A | 5/1994 | Marnay |
| 5,397,364 | A | 3/1995 | Kozak et al. |
| 5,401,269 | A | 3/1995 | Büttner-Janz et al. |
| 5,415,704 | A | 5/1995 | Davidson |
| 5,425,772 | A | 6/1995 | Brantigan |
| 5,425,773 | A | 6/1995 | Boyd et al. |
| 5,443,515 | A | 8/1995 | Cohen et al. |
| 5,484,437 | A | 1/1996 | Michelson |
| 5,505,732 | A | 4/1996 | Michelson |
| 5,507,816 | A | 4/1996 | Bullivant |
| 5,514,180 | A | 5/1996 | Heggeness et al. |
| 5,522,899 | A | 6/1996 | Michelson |
| 5,534,029 | A | 7/1996 | Shima |
| 5,556,431 | A | 9/1996 | Büttner-Janz |
| 5,573,537 | A | 11/1996 | Rogozinski |
| 5,593,409 | A | 1/1997 | Michelson |
| 5,609,635 | A | 3/1997 | Michelson |
| 5,645,596 | A | 7/1997 | Kim et al. |
| 5,658,336 | A | 8/1997 | Pisharodi |
| 5,674,294 | A | 10/1997 | Bainville et al. |
| 5,674,296 | A | 10/1997 | Bryan et al. |
| 5,676,701 | A * | 10/1997 | Yuan et al. ............... 623/17.15 |
| 5,720,748 | A | 2/1998 | Kuslich et al. |
| 5,741,253 | A | 4/1998 | Michelson |
| 5,772,661 | A | 6/1998 | Michelson |
| 5,782,832 | A | 7/1998 | Larsen et al. |
| 5,785,710 | A | 7/1998 | Michelson |
| 5,797,909 | A | 8/1998 | Michelson |
| 5,860,973 | A | 1/1999 | Michelson |
| 5,888,222 | A | 3/1999 | Coates et al. |
| 5,888,226 | A | 3/1999 | Rogozinski |
| 5,899,908 | A | 5/1999 | Kuslich et al. |
| 5,899,941 | A | 5/1999 | Nishijima et al. |
| 5,947,971 | A | 9/1999 | Kuslich et al. |
| 6,004,326 | A | 12/1999 | Castro et al. |
| 6,019,792 | A | 2/2000 | Cauthen |
| 6,039,763 | A | 3/2000 | Shelokov |
| 6,080,155 | A | 6/2000 | Michelson |
| 6,096,038 | A | 8/2000 | Michelson |
| 6,113,637 | A * | 9/2000 | Gill et al. ............... 623/17.15 |
| 6,120,502 | A | 9/2000 | Michelson |
| 6,123,705 | A | 9/2000 | Michelson |
| 6,149,650 | A | 11/2000 | Michelson |
| 6,171,339 | B1 | 1/2001 | Houfburg et al. |
| 6,224,595 | B1 | 5/2001 | Michelson |
| 6,264,656 | B1 | 7/2001 | Michelson |
| 6,270,498 | B1 | 8/2001 | Michelson |
| 6,283,966 | B1 | 9/2001 | Houfburg |
| 6,332,887 | B1 | 12/2001 | Knox |
| 6,368,350 | B1 | 4/2002 | Erickson et al. |
| 6,402,785 | B1 | 6/2002 | Zdeblick et al. |
| 6,413,278 | B1 | 7/2002 | Marchosky |
| 6,416,551 | B1 | 7/2002 | Keller |
| 6,423,095 | B1 | 7/2002 | Van Hoeck et al. |
| 6,440,139 | B2 | 8/2002 | Michelson |
| 6,440,168 | B1 | 8/2002 | Cauthen |
| 6,517,580 | B1 | 2/2003 | Ramadan et al. |
| 6,540,753 | B2 | 4/2003 | Cohen |
| 6,540,785 | B1 | 4/2003 | Gill et al. |
| 6,582,432 | B1 | 6/2003 | Michelson |
| 6,607,558 | B2 | 8/2003 | Kuras |
| 6,682,562 | B2 | 1/2004 | Viart et al. |
| 6,730,127 | B2 * | 5/2004 | Michelson ............... 623/17.16 |
| 6,749,635 | B1 | 6/2004 | Bryan |
| 6,881,228 | B2 | 4/2005 | Zdeblick et al. |
| 6,896,676 | B2 | 5/2005 | Zubok et al. |
| 6,908,484 | B2 | 6/2005 | Zubok et al. |
| 6,994,728 | B2 | 2/2006 | Zubok et al. |
| 6,997,954 | B2 | 2/2006 | Zubok et al. |
| 7,025,787 | B2 | 4/2006 | Bryan et al. |
| 7,115,128 | B2 | 10/2006 | Michelson |
| 2002/0035400 | A1 | 3/2002 | Bryan et al. |
| 2002/0082701 | A1 | 6/2002 | Zdeblick et al. |
| 2002/0143343 | A1 | 10/2002 | Castro |
| 2002/0198533 | A1 | 12/2002 | Geisler et al. |
| 2003/0009224 | A1 | 1/2003 | Kuras |
| 2003/0065394 | A1 | 4/2003 | Michelson |
| 2003/0078661 | A1 * | 4/2003 | Houfburg ............... 623/17.11 |
| 2003/0100951 | A1 | 5/2003 | Serhan et al. |
| 2003/0139816 | A1 | 7/2003 | Michelson |
| 2003/0199982 | A1 | 10/2003 | Bryan |
| 2004/0002758 | A1 | 1/2004 | Landry et al. |
| 2004/0078039 | A1 | 4/2004 | Michelson |
| 2004/0176774 | A1 | 9/2004 | Zubok et al. |
| 2004/0176777 | A1 | 9/2004 | Zubok et al. |
| 2004/0176843 | A1 | 9/2004 | Zubok et al. |
| 2004/0176847 | A1 | 9/2004 | Zubok et al. |
| 2004/0176848 | A1 | 9/2004 | Zubok et al. |
| 2004/0243240 | A1 | 12/2004 | Beaurain et al. |
| 2005/0055029 | A1 | 3/2005 | Marik et al. |
| 2005/0071013 | A1 | 3/2005 | Zubok et al. |
| 2005/0085909 | A1 | 4/2005 | Eisermann |
| 2005/0143821 | A1 | 6/2005 | Zdeblick et al. |
| 2005/0159819 | A1 | 7/2005 | McCormack et al. |
| 2005/0165487 | A1 | 7/2005 | Muhanna et al. |
| 2006/0085077 | A1 | 4/2006 | Cook et al. |

FOREIGN PATENT DOCUMENTS

| | | |
|---|---|---|
| EP | 0 042 271 | 12/1981 |
| EP | 0 179 695 | 4/1986 |
| EP | 0 566 810 | 10/1993 |
| EP | 0 599 419 | 6/1994 |
| EP | 0 699 426 | 3/1996 |
| EP | 0 747 025 | 12/1996 |
| FR | 2 710 519 | 4/1995 |
| FR | 2 718 635 | 10/1995 |
| FR | 2 730 159 | 8/1996 |
| WO | WO 90/00037 | 1/1990 |
| WO | WO 91/13598 | 9/1991 |
| WO | WO 92/14423 | 9/1992 |
| WO | WO 93/10725 | 6/1993 |
| WO | WO 94/04100 | 3/1994 |
| WO | WO 94/26893 | 11/1994 |
| WO | WO 95/08306 | 3/1995 |
| WO | WO 95/31947 | 11/1995 |
| WO | 96/27345 A2 | 9/1996 |
| WO | 99/53871 A1 | 10/1999 |
| WO | WO-0164142 | 9/2001 |
| WO | WO-2006116851 | 11/2006 |

OTHER PUBLICATIONS

Final Office Action for U.S. Appl. No. 12/132,919 mailed Mar. 23, 2011.

Non-Final Office Action for U.S. Appl. No. 12/132,919 mailed Oct. 18, 2010.

* cited by examiner

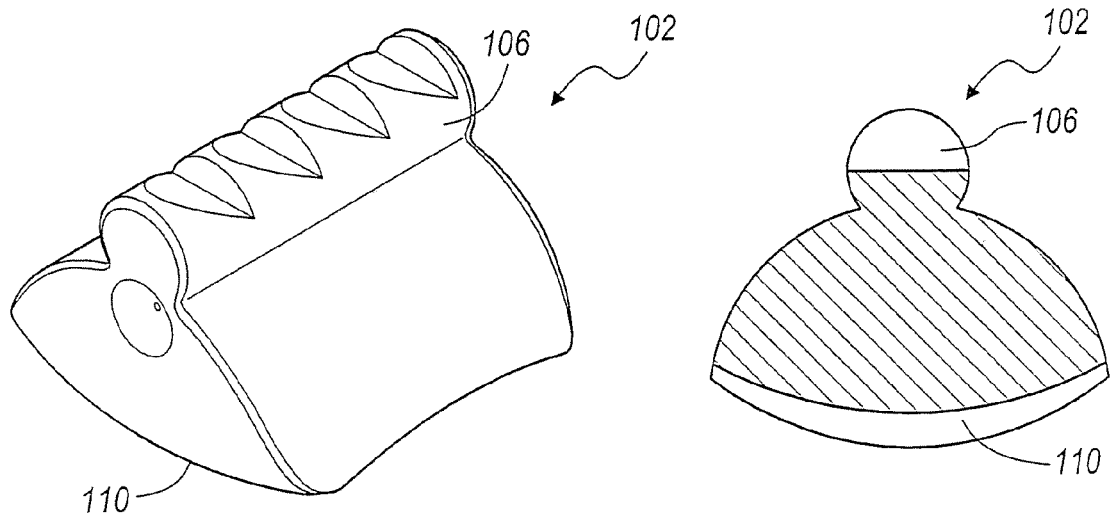
FIG. 12A
FIG. 12B
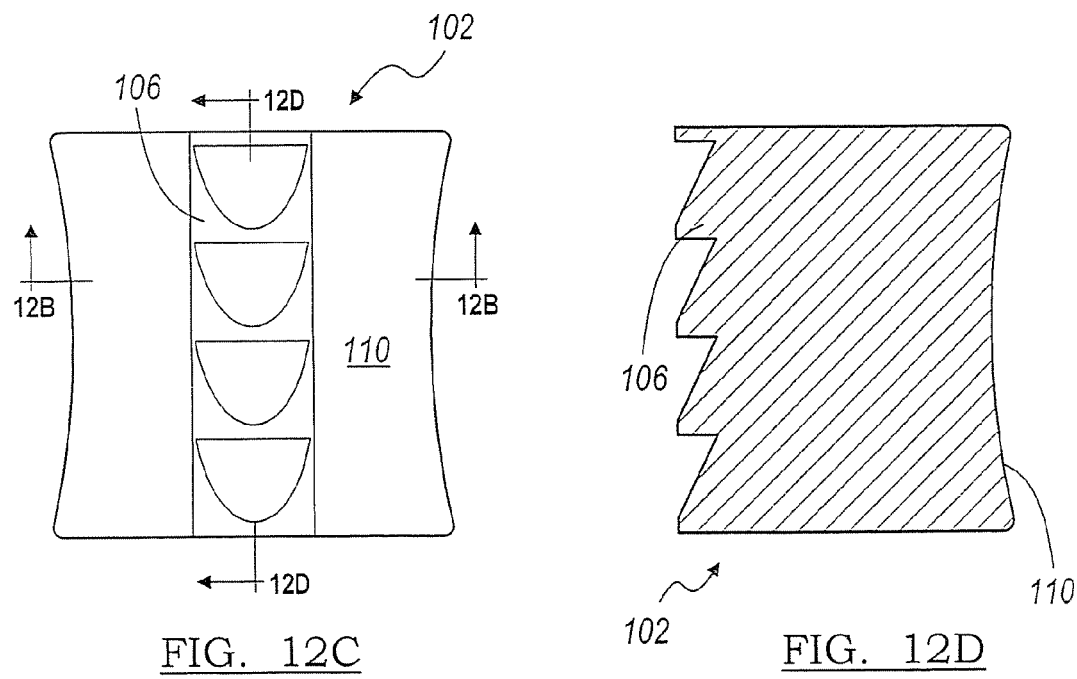
FIG. 12C
FIG. 12D

INTERVERTEBRAL IMPLANT AND ASSOCIATED METHOD

CROSS-REFERENCE TO RELATED APPLICATIONS

This application is a continuation-in-part of U.S. patent application Ser. No. 11/248,101 filed on Oct. 12, 2005. This application claims the benefit of U.S. Provisional Application No. 60/619,842, filed on Oct. 18, 2004. The disclosures of the above applications are incorporated herein by reference.

INTRODUCTION

The spinal column provides the main support for the body and is made of thirty-three individual bones called vertebrae. There are twenty-four moveable vertebrae in the spine, with the remaining being fused. Each vertebra includes an anterior vertebral body, a posterior vertebral arch that protects the spinal cord, and posterior processes extending from the vertebral arch. The vertebral body is drum-shaped and includes superior and inferior endplates. The moveable vertebrae are stacked in series and are separated and cushioned by anterior intervertebral discs.

Each vertebral body transmits loads to adjacent bodies via an anterior intervertebral disc and two posterior facets. The intervertebral disc is composed of an outer fibrous ring called the annulus. Nucleus pulposus is a gel-like substance housed centrally within the annulus and sandwiched between the endplates of the adjacent vertebral bodies. The annulus operates as a pressure vessel retaining an incompressible fluid. In a healthy disc, the nucleus pulposus acts as hard sphere seated within the nuclear recess (fossa) of the vertebral endplates. This sphere operates the fulcrum (nuclear fulcrum) for mobility in the spine. Stability is achieved by balancing loads in the annulus and the facet joints.

Degenerative disc disease affects the physiology of the disc and may be caused by aging, protrusion of the nucleus into the annulus or endplates, trauma or other causes. The result in either case may produce a reduction of disc height, which in turn, alters the loading pattern in the facets causing symptomatic degeneration of the facet joints, thus reducing stability, and compressing nerves branching out of the spinal column.

Examples of surgical treatments of degenerative disc disease include spinal arthroplasty with total disc replacement that requires a full discectomy or with nucleus replacement that disrupts the annulus. Although these devices can be effective for their intended purposes, it is still desirable to have implants and associated methods that are less disruptive and provide the required degree of stability and mobility to the affected region of the spine.

SUMMARY

The present teachings provide an intervertebral implant and associated method. The intervertebral implant comprises superior and inferior components mutually articulating to replicate natural spine movement.

In one aspect, the present teachings provide an intervertebral implant that can include a first component having a first articulating surface and a first bone engagement surface for engaging a first vertebra, and a second component having a second articulating surface and a second bone engagement surface for engaging a second vertebra adjacent to the first vertebra. The first and second articulating surfaces can articulate with each other for substantially replicating a natural spinal movement including torsion, extension/flexion, and lateral bending. The first and second bone engagement surfaces can define an outer surface substantially shaped as an envelope of two intersecting cylinders.

The present teaching provide a surgical kit that includes an insertion cannula defining a longitudinal bore, an intervertebral implant pre-loaded within the longitudinal bore, and a retainer for temporarily retaining the intervertebral implant within the longitudinal bore.

The present teachings also provide a method for inserting an intervertebral implant in a disc space. The method includes providing an insertion cannula having a longitudinal bore, preloading the intervertebral implant within the longitudinal bore of the insertion cannula in a substantially fixed position, supporting the insertion cannula relative to the disc space, releasing the intervertebral implant from the substantially fixed position, and implanting the intervertebral implant into the disc space.

The present teachings also provide a surgical device that includes an insertion cannula defining a longitudinal bore and a retainer integral to the cannula, an intervertebral implant matingly pre-loaded within a distal portion of the longitudinal bore and releasably held by the retainer.

The present teachings further provide a surgical device that includes a modular intervertebral implant having an outer surface substantially shaped as an envelope of five cylinders.

The present teachings further provide a spacer guide adapted for supporting a plurality of tools used for preparing vertebral endplates for receiving an intervertebral implant. The spacer guide can include a tool-supporting elongated shaft, a depth stop flange at a distal portion of the shaft, wherein the flange defines a plurality of guiding cutouts for guiding the plurality of tools, and a frame extending from the flange and receivable into the intervertebral disc space. The frame can include a distal member operable as a stop for the plurality of tools.

The present teachings also provide a cutting tool guide for vertebral endplates for receiving an intervertebral implant. The cutting tool guide can include a cannulated body defining a plurality of guiding bores, wherein each guiding bore is configured for supporting a cutting tool used to prepare an opening in the endplates for receiving a corresponding portion of the intervertebral implant. The cutting tool guide can include a boss extending distally from the body. The boss can include a plurality of guiding grooves aligned with the corresponding bores of the body.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 12A is an isometric view of a superior component of a toroidal intervertebral implant according to the present teachings;

FIG. 12B is a coronal sectional view of the superior component of the toroidal intervertebral implant of FIG. 12A;

FIG. 12C is an axial view of the superior component of the toroidal intervertebral implant of FIG. 12A;

FIG. 12D is a sagittal sectional view of the superior component of the toroidal intervertebral implant of FIG. 12A;

DESCRIPTION OF VARIOUS ASPECTS

The following description is merely exemplary in nature and is in no way intended to limit the invention, its application, or uses. For example, although the present teachings are illustrated for intervertebral disc implants, the present teachings can be used for other spine implants, such as intervertebral spacers, for example.

Figure 1:
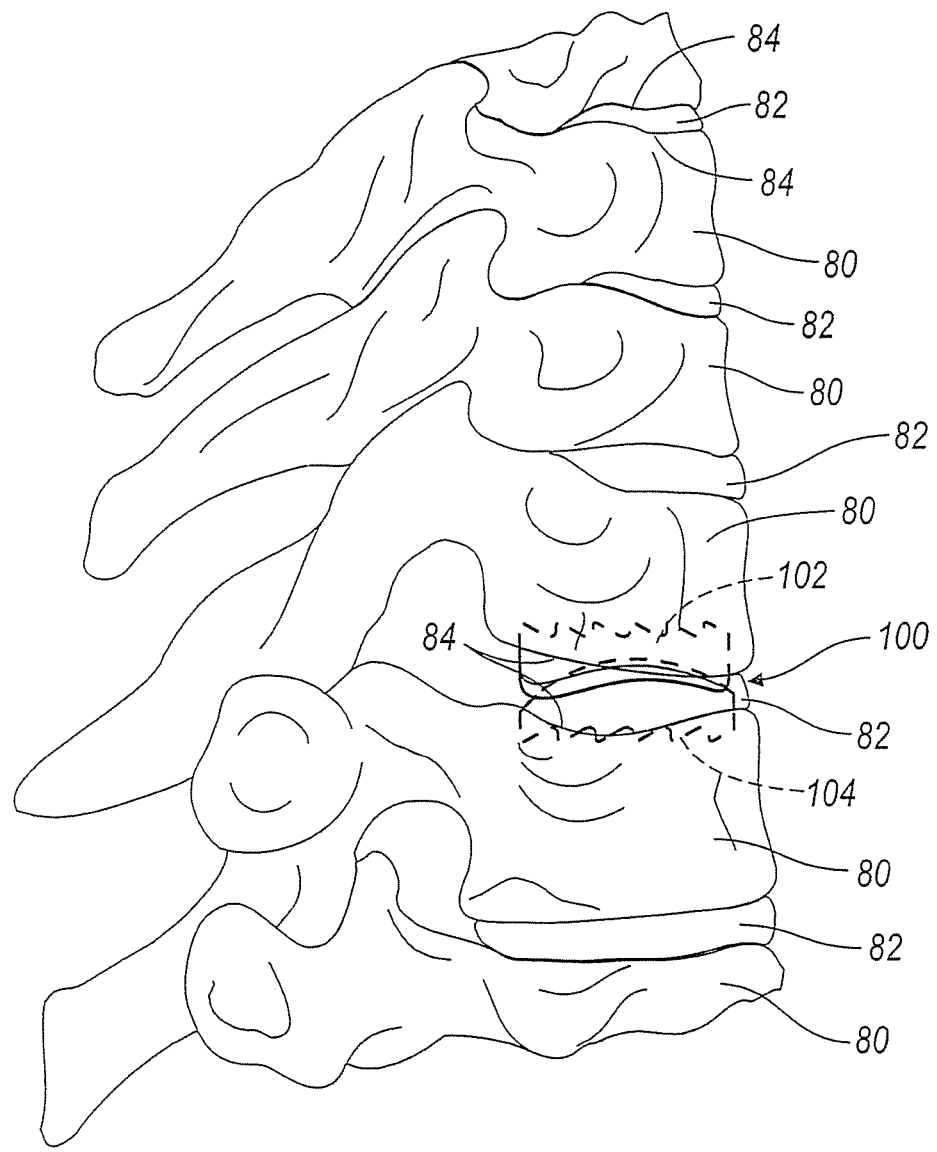
FIG. 1 is a sagittal sectional view of an intervertebral implant according to the present teachings, shown implanted in a spine.
Figure 1A:
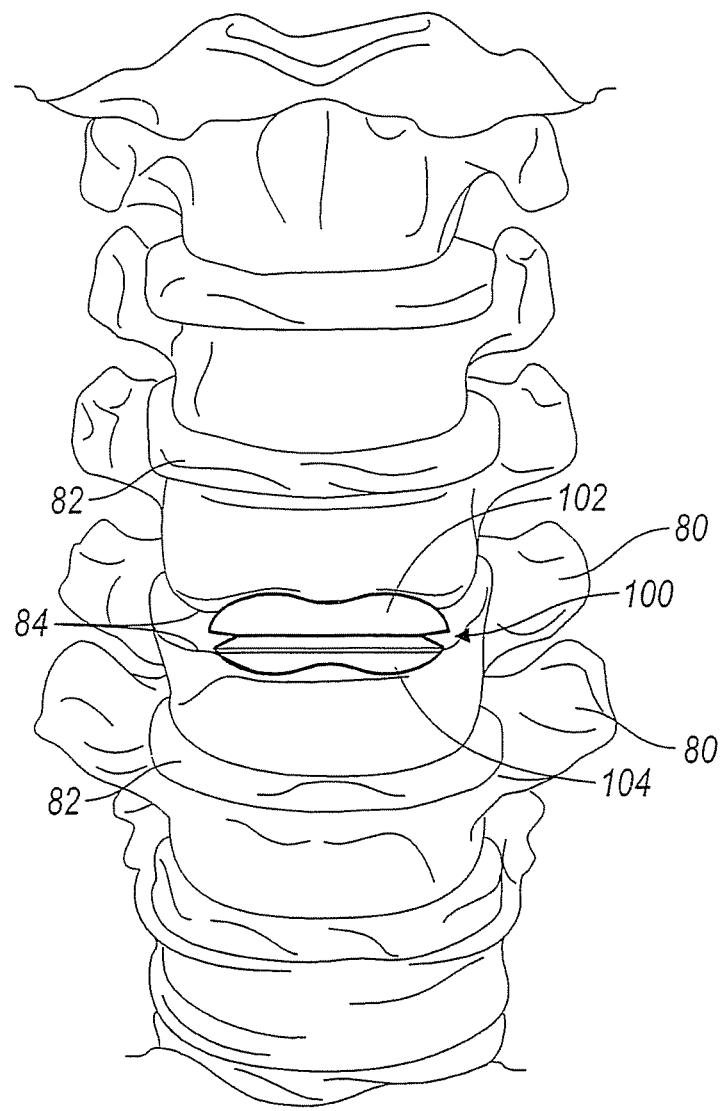
FIG. 1A is a coronal end view of an intervertebral implant according to the present teachings, shown implanted in a spine.

Referring to FIGS. 1 and 1A, exemplary intervertebral implant 100 according to the present teachings are illustrated as implanted between two adjacent vertebral bodies 80 having endplates 84. The intervertebral implant 100 can be nested between the endplates 84 of the vertebral bodies 80 and may be partially surrounded by a portion of a natural intervertebral disc 82 replacing the nucleus thereof. Alternatively, the entire natural intervertebral disc 82 can be removed and replaced by the intervertebral implant 100.

The intervertebral implant 100 can be a multiple component implant that includes superior and inferior components 102, 104 configured for mutual articulation that can replicate the primary modes of motion in the spine and any combination thereof. The superior and inferior articulation components 102, 104 can be designed to resurface the adjacent endplates 84 at the nuclear fulcrum and re-establish disc height to its original dimension. Accordingly, improved motion and increased stability can be established in the region of the intervertebral implant 100 without dependence on the integrity of the endplate cartilage.

Figure 3:
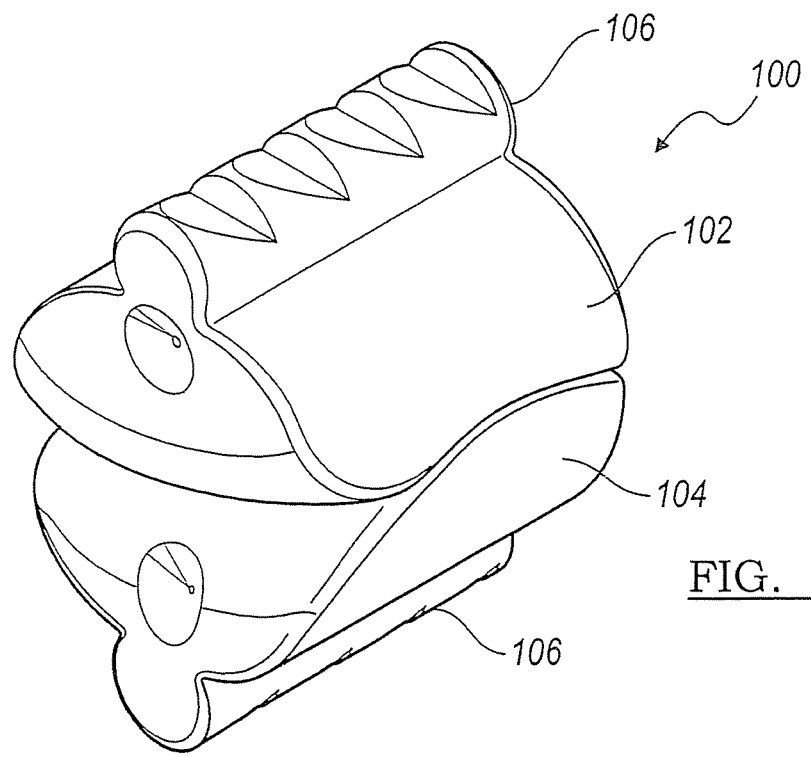
FIG. 3 is an isometric view of the intervertebral implant of FIG. 2.
Figure 5:
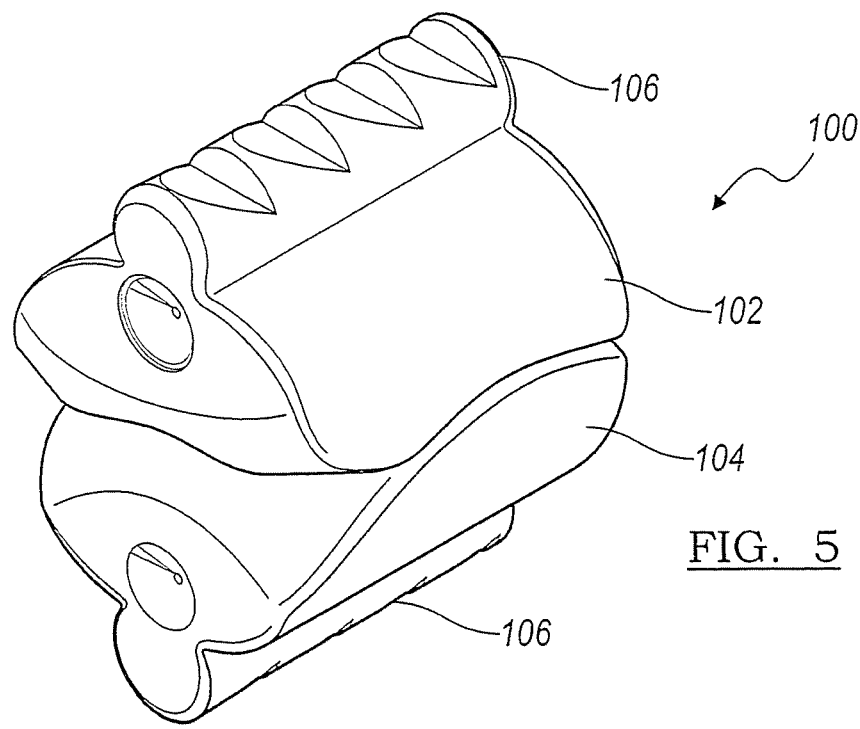
FIG. 5 is an isometric view of the intervertebral implant of FIG. 4.

The articulation between the inferior and superior articulation components 102, 104 of the intervertebral implant 100 can substantially replicate natural spinal movement. Two exemplary aspects of such articulation between the inferior and superior articulation components 102, 104 of the intervertebral implant 100 are illustrated in FIGS. 3 and 5, and referred respectively herein as "toroidal" and "spherical" intervertebral implant 100 for reasons that are discussed below. The articulation illustrated in FIG. 1A, and FIGS. 17A-17C is of the spherical type, although toroidal type articulation can also be used with the intervertebral implant 100 illustrated in these figures.

Figure 9A:
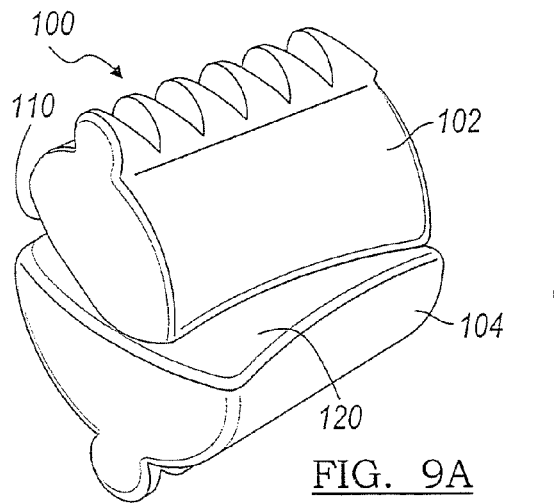
FIGS. 9A, 9B and 9C illustrate exemplary articulation motions including torsion, extension/flexion, and lateral bending, respectively, for a toroidal intervertebral implant according to the present teachings.
Figure 9B:
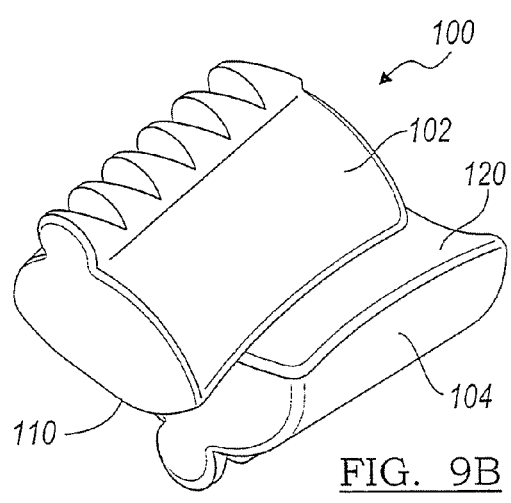
Figure 9C:
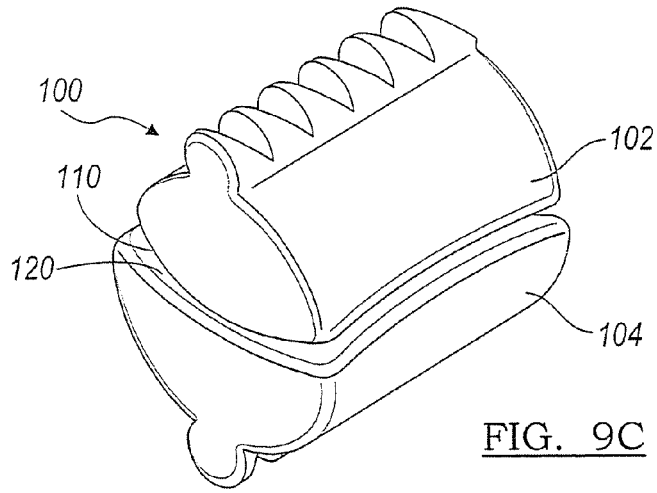

More particularly, FIGS. 9A, 9B, and 9C illustrate respectively torsion, extension/flexion, and lateral bending for the toroidal intervertebral implant 100 of FIG. 3, and FIGS. 15A, 15B, and 15C illustrate respectively torsion, extension/flexion, and lateral bending for the spherical intervertebral implant 100 of FIG. 5.

Referring to FIGS. 3 and 5, each of the superior and inferior components 102, 104 can include a serrated rack 106 for preventing migration of the intervertebral implant 100 relative to the vertebral bodies 80. It will be appreciated that other anchoring structures known in the art can be used for securing the intervertebral implant 100 against migration, such as, for example, projections of various geometric shapes engaging corresponding recesses in the endplates, surface treatment promoting frictional resistance including porous coatings that promote bone growth, and other structures.

Figure 14:
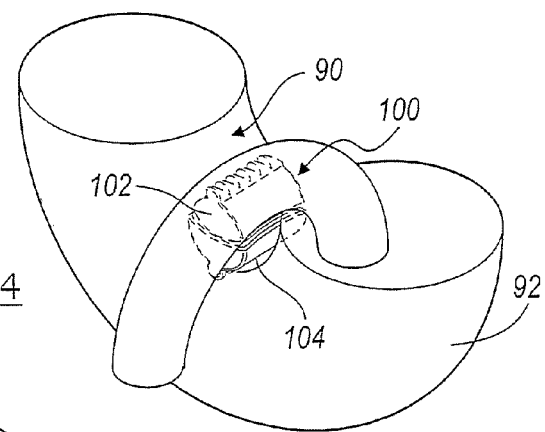
FIG. 14 is a conceptual illustration of constructing a toroidal intervertebral implant according to the present teachings.
Figure 15A:
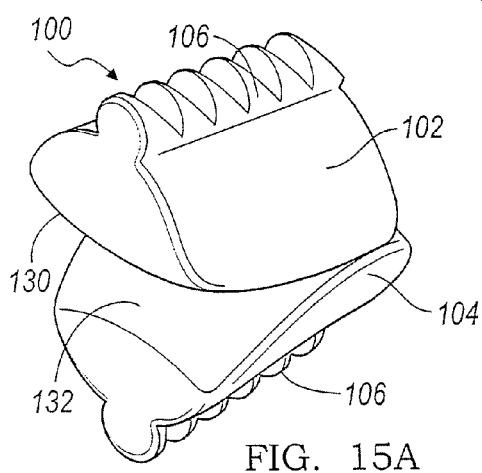
FIGS. 15A, 15B and 15C illustrate exemplary articulation motions for a spherical intervertebral implant according to the present teachings
Figure 15B:
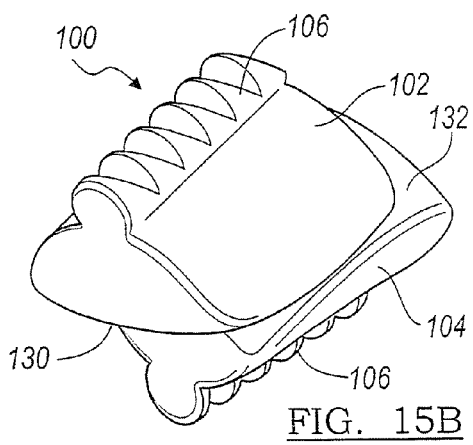
Figure 15C:
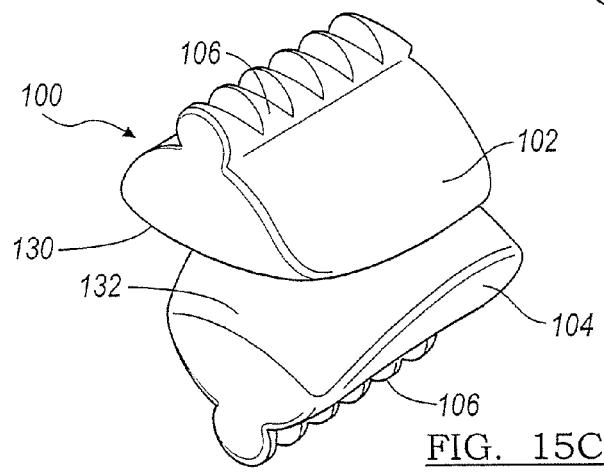

Referring to FIGS. 2, 3, and 12-14, the toroidal intervertebral implant 100 can be created, for example, by removing a cylinder at the contact between two tori 90, 92, as conceptually illustrated in FIG. 14. Referring to FIG. 12C, the superior component 102 includes an articulating surface 110. The articulating surface 110 of the superior component 102 includes a convex radius in the coronal plane, as shown in FIG. 12B, and a concave radius in the sagittal plane, as shown in FIG. 12D. Referring to FIG. 13C, the inferior component 104 includes an articulating surface 120. The articulating surface 120 of the inferior component 104 includes a concave radius in the coronal plane, shown in FIG. 13B, and a convex radius in the sagittal plane, shown in FIG. 13D. In the sagittal plane, the superior articulating surface 110 can have a larger radius of curvature than the inferior articulating surface 120. In one aspect, in the coronal plane, the convex superior articulating surface 110 can be defined by a shallow "V" having a tip that is rounded with a fillet radius. The toroidal intervertebral implant 100 can include an A/P taper to minimize subchondral bone removal.

Figure 4:
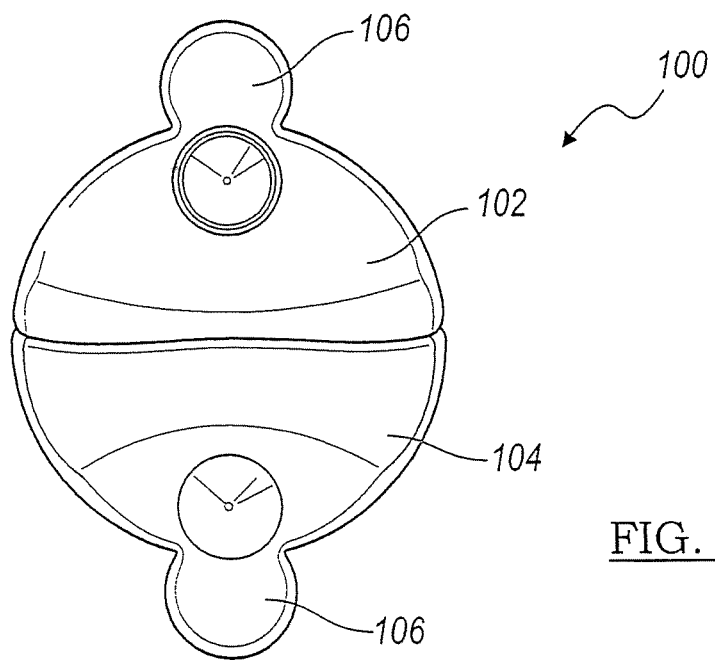
FIG. 4 is a coronal end view of a spherical intervertebral implant according to the present teachings.
Figure 16A:
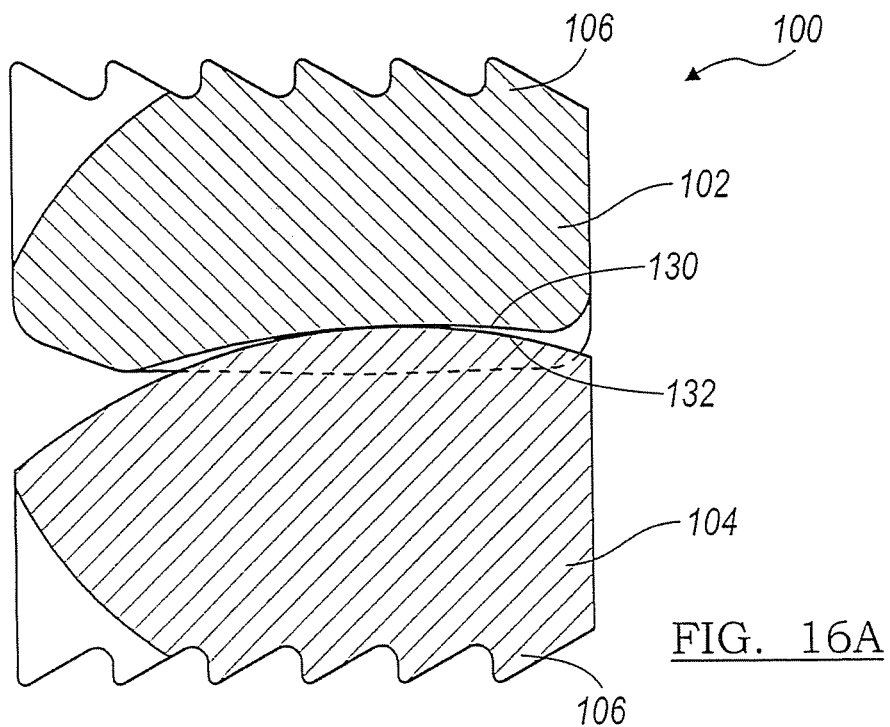
FIG. 16A is a sagittal sectional view of a spherical intervertebral implant according to the present teachings.
Figure 16B:
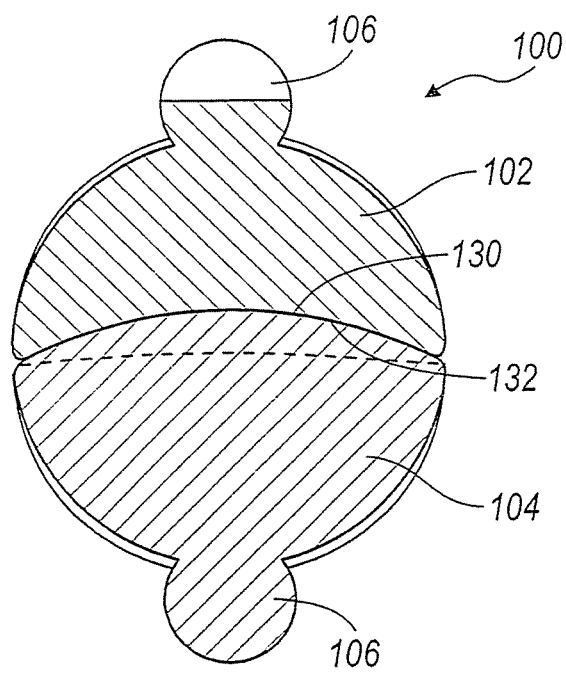
FIG. 16B is a coronal sectional view of the spherical intervertebral implant of FIG. 16A.

Referring to FIGS. 4, 5, and 16, the superior and inferior components 102, 104 of the spherical intervertebral implant 100 include respective articulating surfaces 130, 132. The articulating surface 132 of the inferior component 104 is convex and at least partially spherical. The articulating surface 130 of the superior component 102 is concave. In the sagittal plane, shown in FIG. 16A, the radius of the superior component 102 can be greater than the radius of the inferior component 104 to allow for anterior-posterior (A/P) translation. The apex of the articulating surfaces 130, 132 is indicated by axis A-A in FIG. 16A, and can be offset two thirds posteriorly to align the articulating fulcrum of the spherical intervertebral implant 100 with the nuclear recess in the vertebral endplates 84. The radius of curvature of the inferior articulating surface 132 can be larger anteriorly to the apex (axis A-A) than the radius of curvature posteriorly to the apex, as illustrated in FIG. 16A. The spherical intervertebral implant 100 can include an A/P taper to minimize subchondral bone removal. In the coronal plane, shown in FIG. 16B, the curvatures of the articulating surfaces 130, 132 are congruent with equal radii to maximize contact area.

Figure 17A:
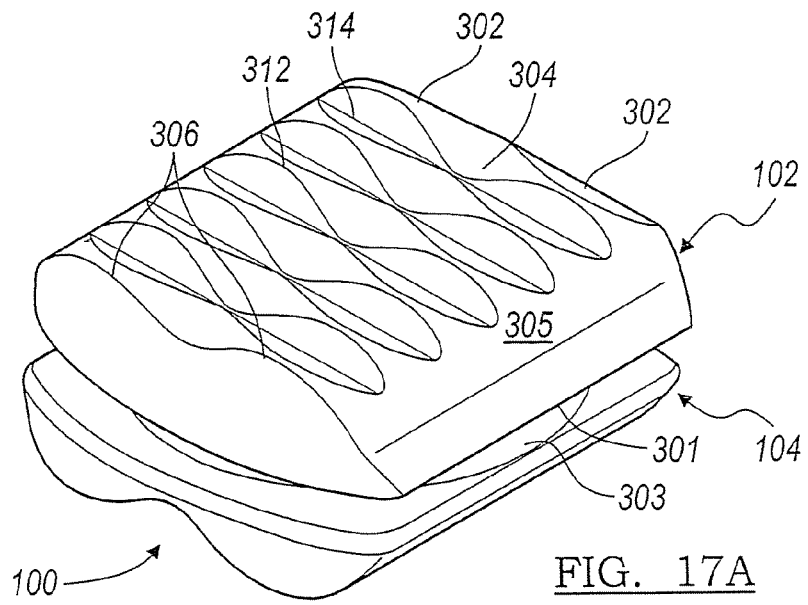
FIG. 17A is an isometric view of an intervertebral implant according to the present teachings.
Figure 17B:
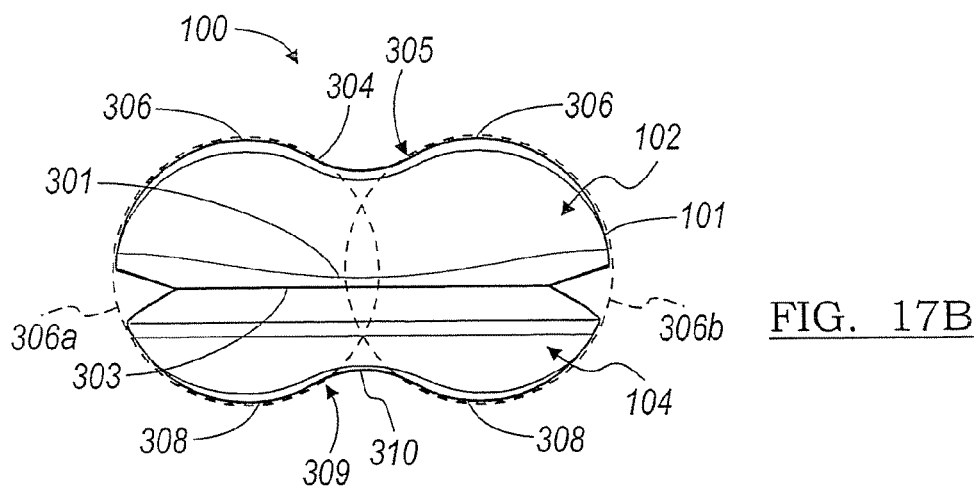
FIG. 17B is a front view of an intervertebral implant according to the present teachings.

The intervertebral implant 100 illustrated in FIGS. 1A, and 17A-17C, can have a spherical or toroidal type of articulation, as discussed above, although spherical articulating surfaces 301, 303 are illustrated. The superior and inferior articulating components 102, 104 can include respective superior and inferior bone engagement surfaces 305, 309. The superior and inferior bone engagement surfaces 305, 309 can include pairs of separate outwardly convex end portions 306, 308 connected with outwardly concave intermediate portions 304, 310, respectively. The superior and inferior bone engagement surfaces 305, 309 can be formed, for example, by two cylinders 306a, 306b of circular cross-section, which can be intersecting, as illustrated in FIG. 17B in dotted lines. Accordingly, the outer surface 101 of the bi-cylindrical intervertebral implant can be defined as a curved surface enveloping the intersecting cylinders 306a, 306b. Non-intersecting cylinders can also be used in other aspects.

Each of superior and inferior bone engagement surfaces 305, 309 can include bone-engagement formations 302. The bone engagement formations 302 can be arranged in parallel rows on the convex end portions 306, 308. The engagement formations 302 can include crests 312 and grooves 314. Both crests 312 and grooves 314 can be designed with smooth rounded profiles balancing effective bone engagement while reducing potential damage by avoiding sharp edges.

Figure 6:
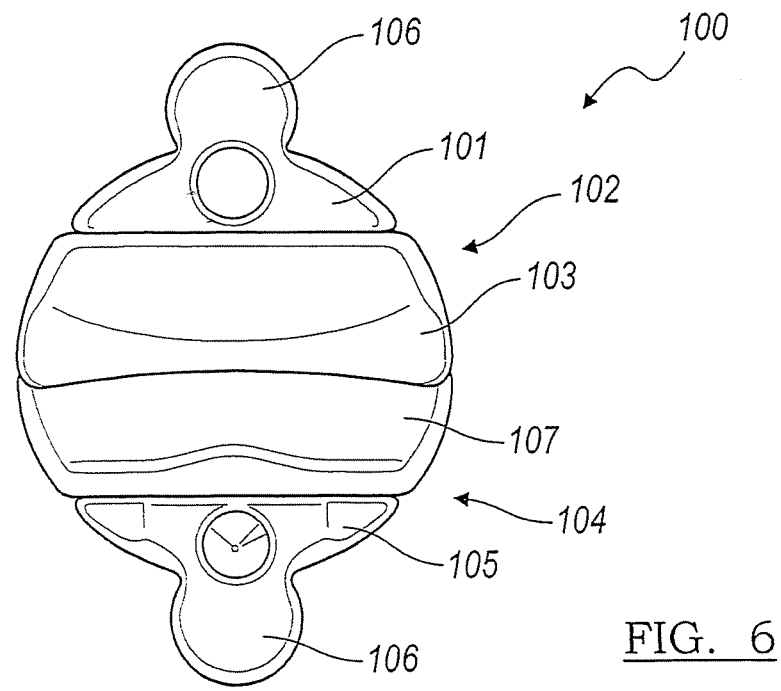
FIG. 6 is a coronal end view of an intervertebral implant according to the present teachings.
Figure 7:
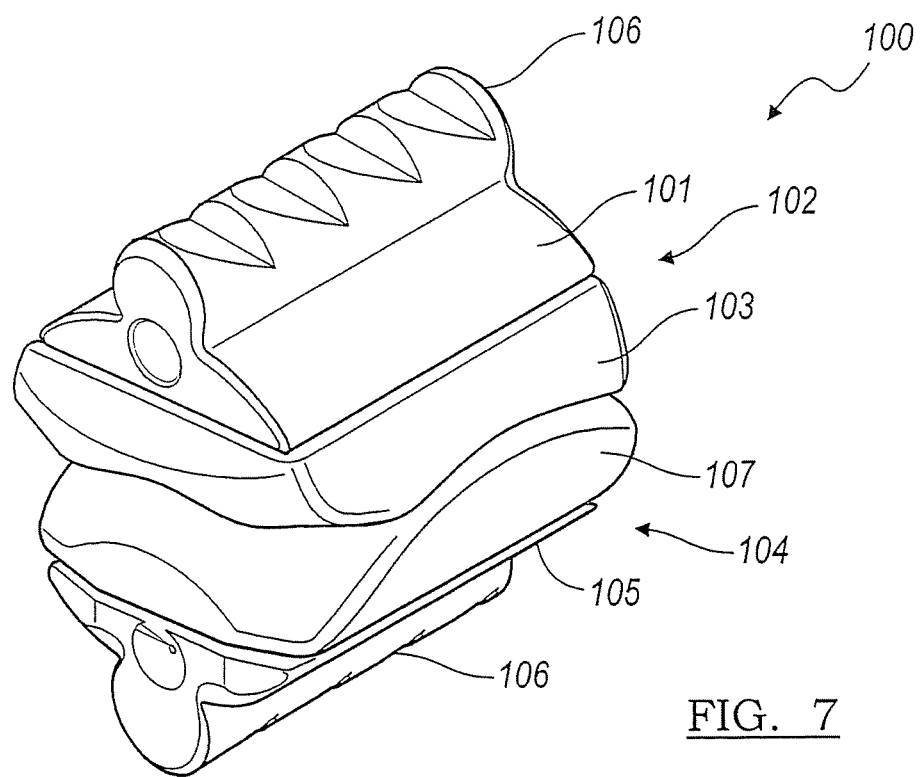
FIG. 7 is an isometric view of the intervertebral implant of FIG. 6.

The intervertebral implant 100 can be manufactured from biocompatible materials, such as, for example, cobalt chromium alloy, titanium alloys or other metals, pyrolytic carbon, and other materials. It can also be constructed from a combination of materials. Referring to FIGS. 6 and 7, each superior component 102 can include an outer portion 101 made of titanium, titanium alloy or other biocompatible metal or alloy, and an articulating portion 103 made of pyrolytic carbon. Similarly, each inferior component 104 can include an outer portion 105 made of titanium, titanium alloy or other biocompatible metal or alloy, and an articulating portion 107 made of pyrolytic carbon. It should be noted that although the intervertebral implant 100 illustrated in FIGS. 6 and 7 is of the spherical type, the toroidal intervertebral implant 100 can also be manufactured by a similar combination of materials. It will be appreciated that other biocompatible metallic or non-metallic materials can also be used.

Figure 2:
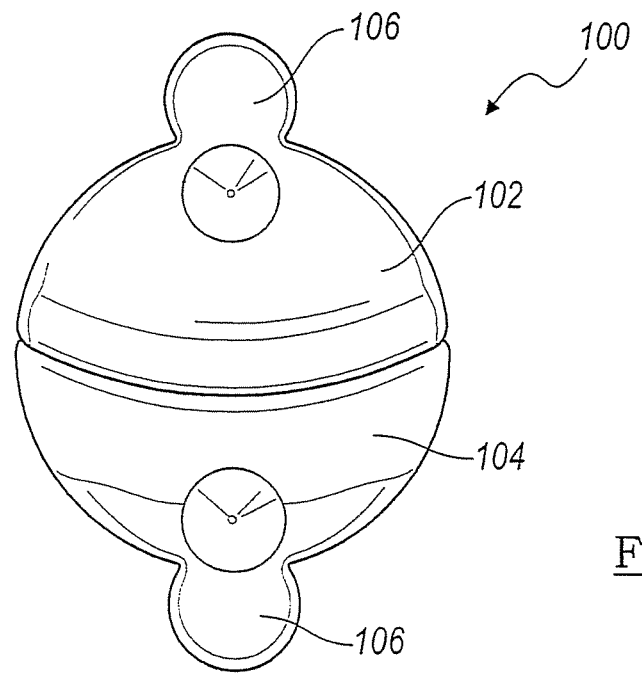
FIG. 2 is a coronal end view of a toroidal intervertebral implant according to the present teachings.
Figure 17C:
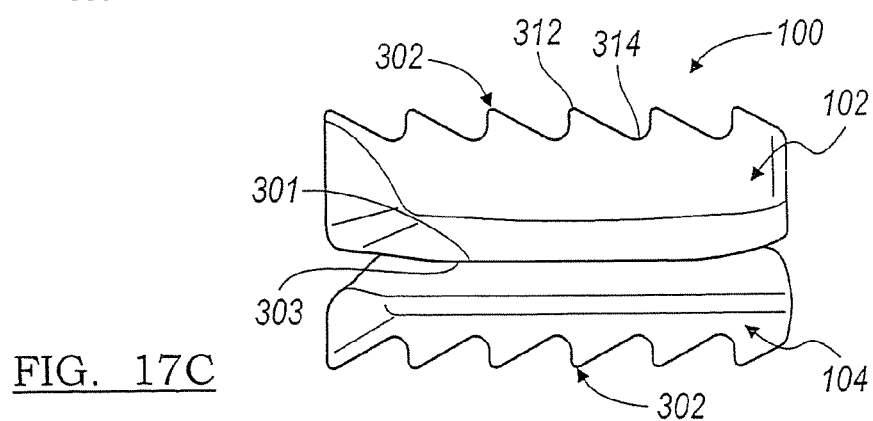
FIG. 17C is a side view of an intervertebral implant according to the present teachings.

It will be appreciated that the terms "toroidal" and "spherical" are in reference to the relative articulation of the superior and inferior components 102, 104, and that the overall shape of the intervertebral implant 100 can be substantially cylindrical, as illustrated 2, 3 and 6, or bi-cylindrical, as illustrated in FIGS. 17A-17C. Referring to FIGS. 2, 3, and 6, the coronal section of the intervertebral implant 100 can include a substantially circular central section defined by the superior and inferior components 102, 104 and two partially circular extensions defined by the serrated racks 106. It will be appreciated, however, that particular features associated with particular illustrations are merely exemplary. Accordingly, features that illustrated in one exemplary embodiment can also be used in other embodiments, although not particularly illustrated.

Figure 8:
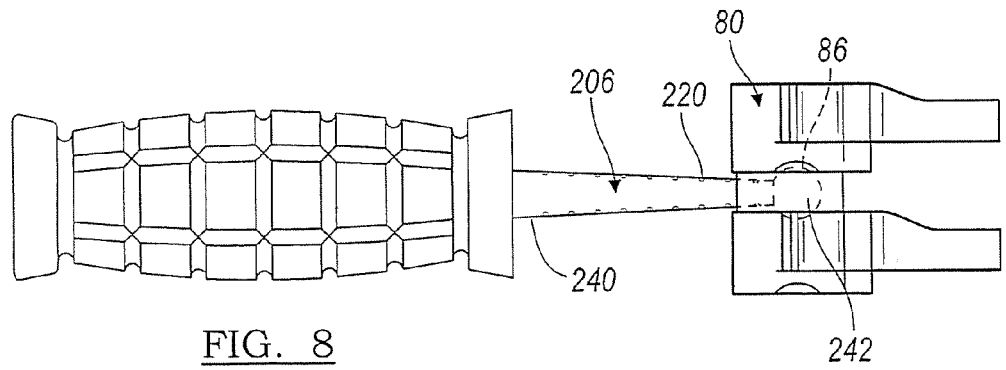
FIG. 8 is a side view of a probe shown in use for locating a nuclear recess.

The method of implanting the intervertebral implant 100 and associated instruments is described with particular reference to FIGS. 18-25, and with additional reference to FIG. 8, for implanting the intervertebral implant 100 illustrated in FIGS. 17A-17C.

Figure 18:
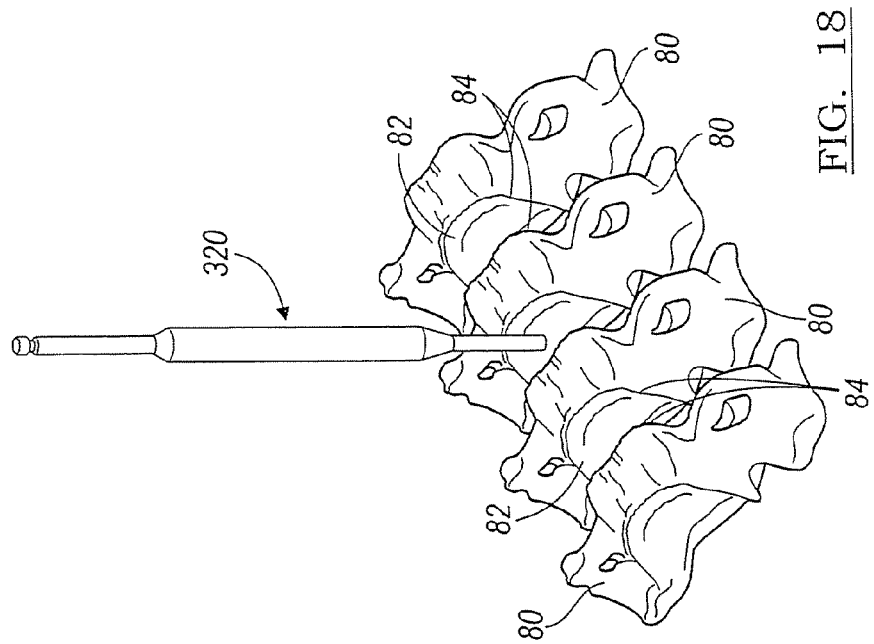

Preparatory to the surgical procedure, the patient can be positioned such that there is a natural amount of lordosis, if the surgeon prefers to perform a discectomy under distraction. The affected segment of the spine can be exposed anteriorly. A small annulotomy/discectomy can be performed, excising the nucleus and all degenerated material. Referring to FIG. 18, the annulotomy/discectomy can be sized for receiving a centering shaft 320 or other centering/locating instrument, such as, for example, a fossa locator 206 illustrated in FIG. 8. The fossa locator 206 can be inserted into the natural disc space to locate the nuclear recess 86. The fossa locator 206 can include a removable handle 208, including a shaft 240 and a distal tip 242 that can be cylindrical in shape. The fossa locator 206 can be inserted until the tip 242 engages the nuclear recess 86. Graduated markings 220 on the shaft 240 of the fossa locator 206 indicate the depth required for subsequent drilling and broaching. The handle 208 from the fossa locator 206 can then be removed, such that the shaft 240 of the fossa locator can also function as a centering shaft, such as the centering shaft 320 illustrated in FIG. 18.

Figure 19:
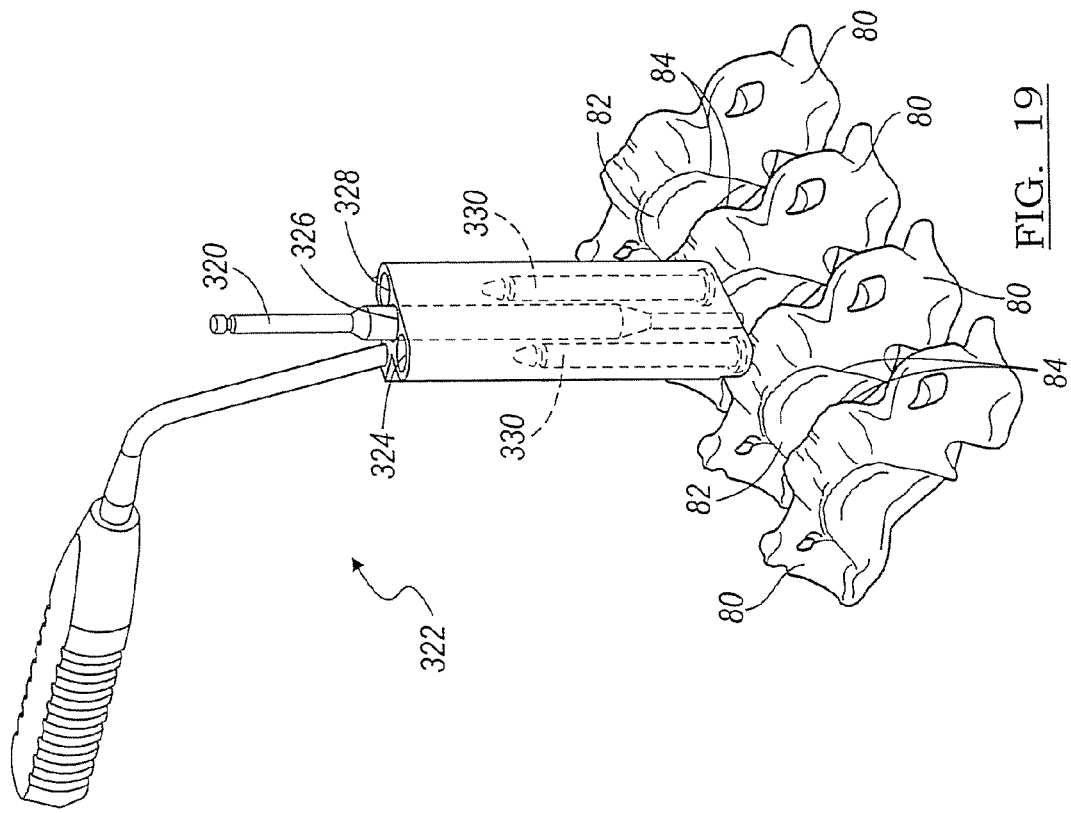
FIGS. 18-30 illustrate a method of implanting an intervertebral implant according to the present teachings.
Figure 20:
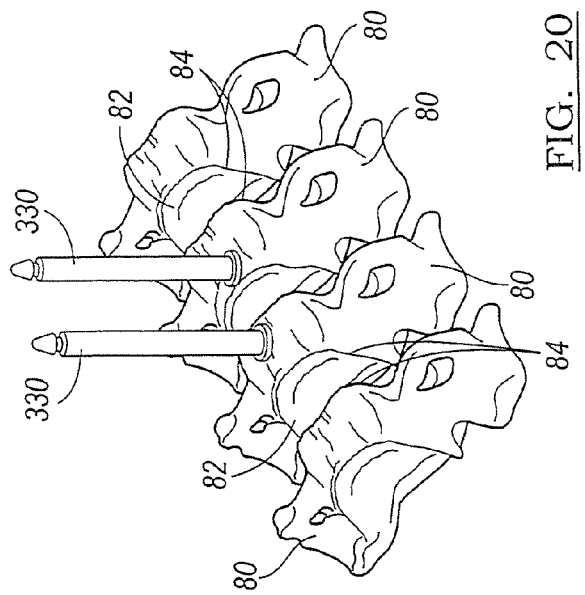
Figure 23:
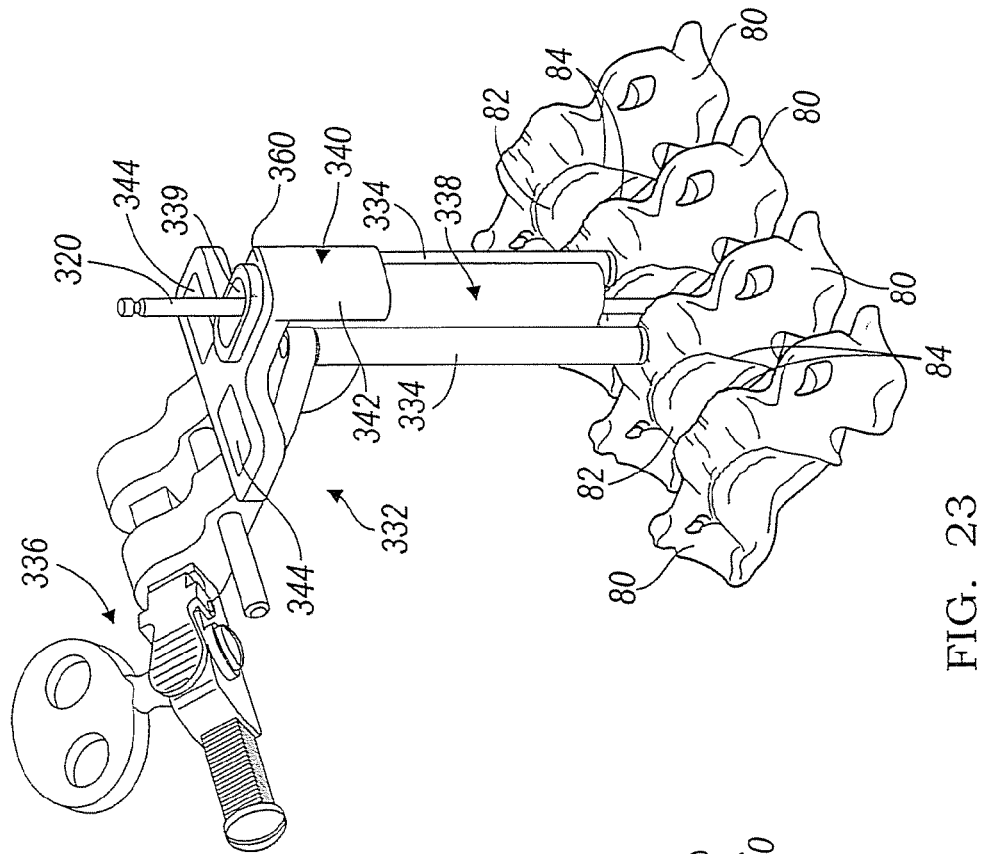
Figure 22:
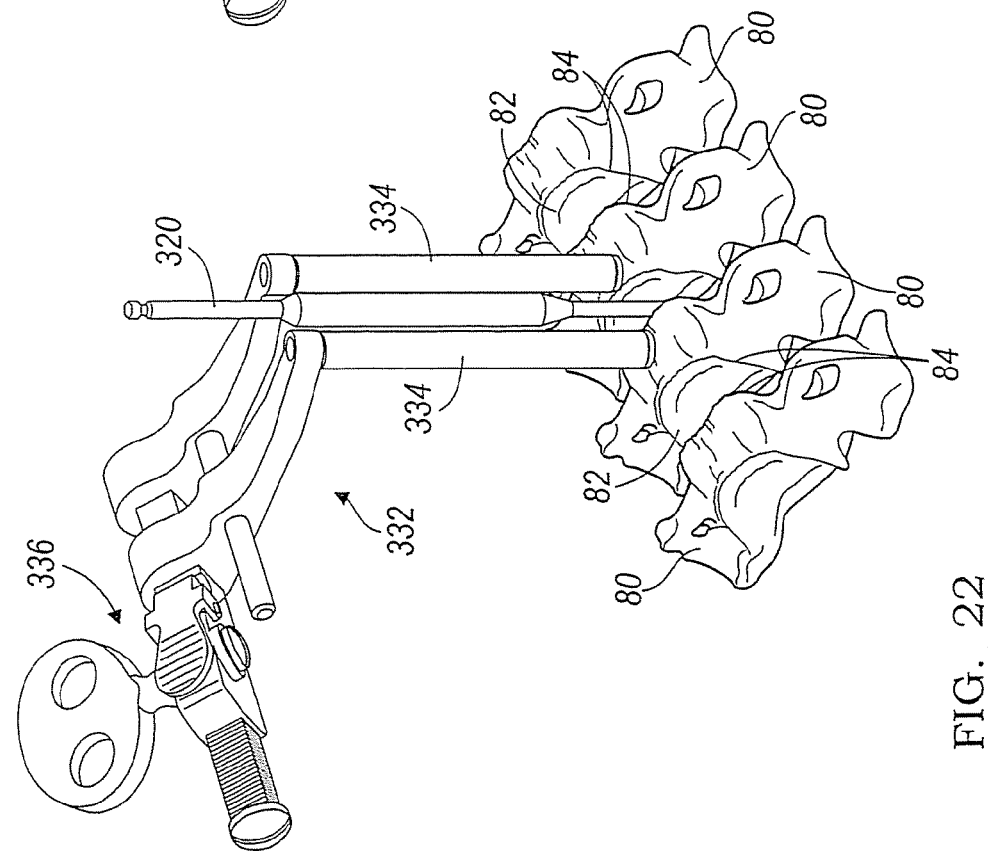
Figure 25:
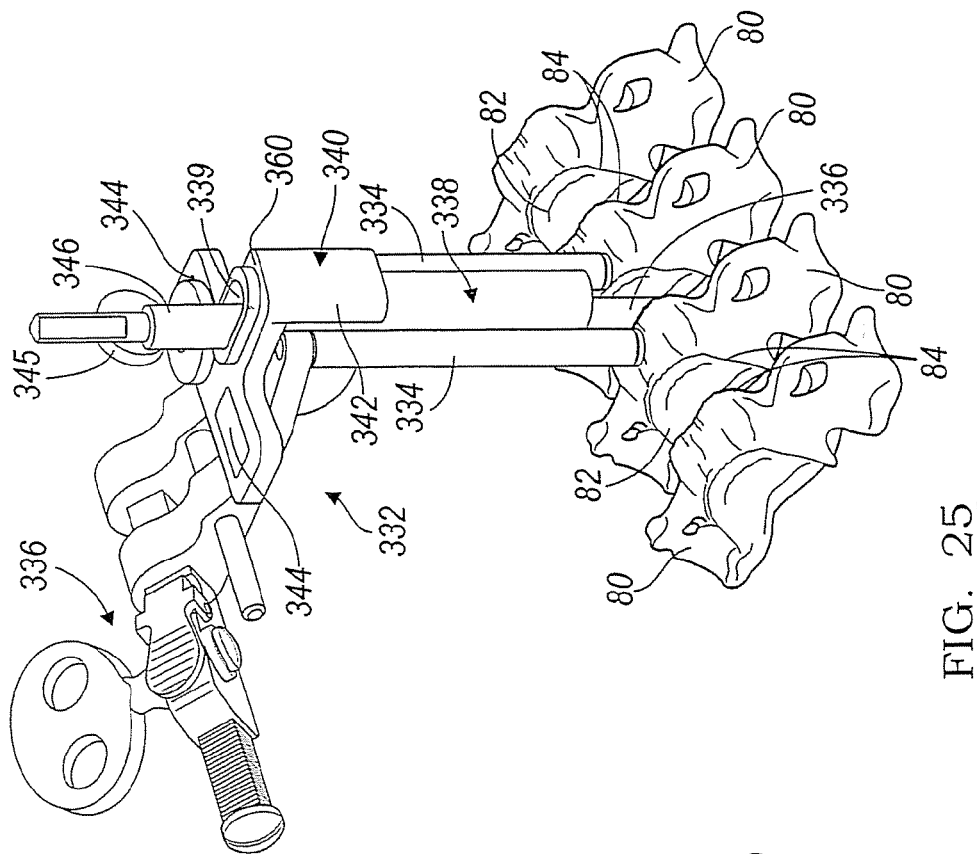
Figure 33:
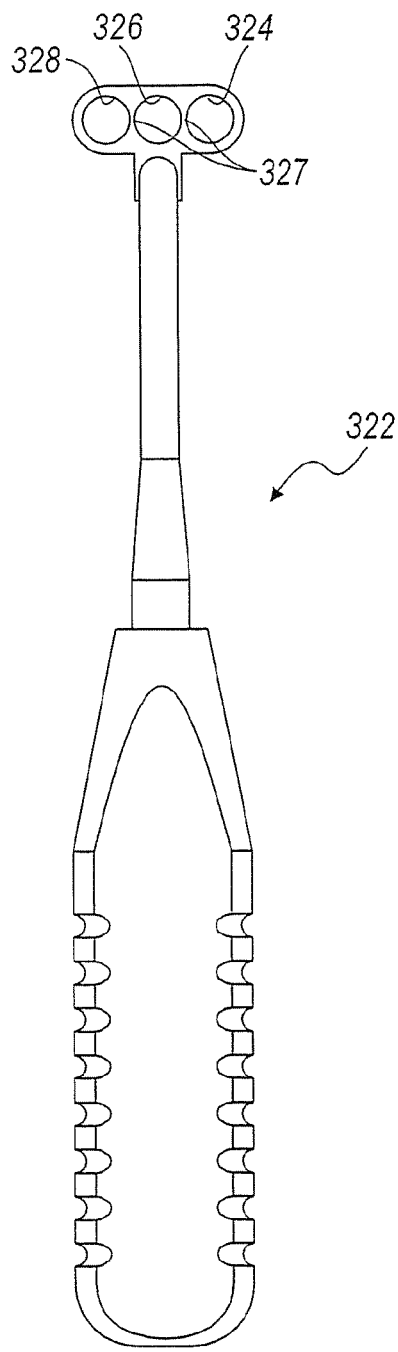
FIG. 33 is a plan view of a distraction pin guide according to the present teachings.

Referring to FIGS. 19 and 33, a distraction pin guide 322 can be placed over the centering shaft 320. The distraction pin guide 322 can include a pair of side longitudinal openings/lumens 324, 328 and an intermediate longitudinal opening/lumen 326 positioned therebetween. The intermediate longitudinal opening 326 can be defined by an internal wall structure 327 that fully separates the intermediate opening 326 from the side openings 324, 328, as illustrated in FIG. 33, which shows the intermediate opening 326 and the side openings 324, 328 as three non-intersecting circles. It will be appreciated that other wall structures can also be used, including wall structures that allow at least partial communication between the intermediate opening 326 and the side openings 324, 328. The centering shaft 320 can be received in the intermediate opening 326, which is appropriately sized. A pair of self-drilling distraction pins or other anchoring pins 330 can be inserted through the side openings 322, 328 for anchoring into adjacent vertebrae on opposite sides of the disc space. The centering shaft 320 and the distraction pin guide 322 can be removed after placement of the distraction pins 330, as illustrated in FIG. 20.

Figure 21:
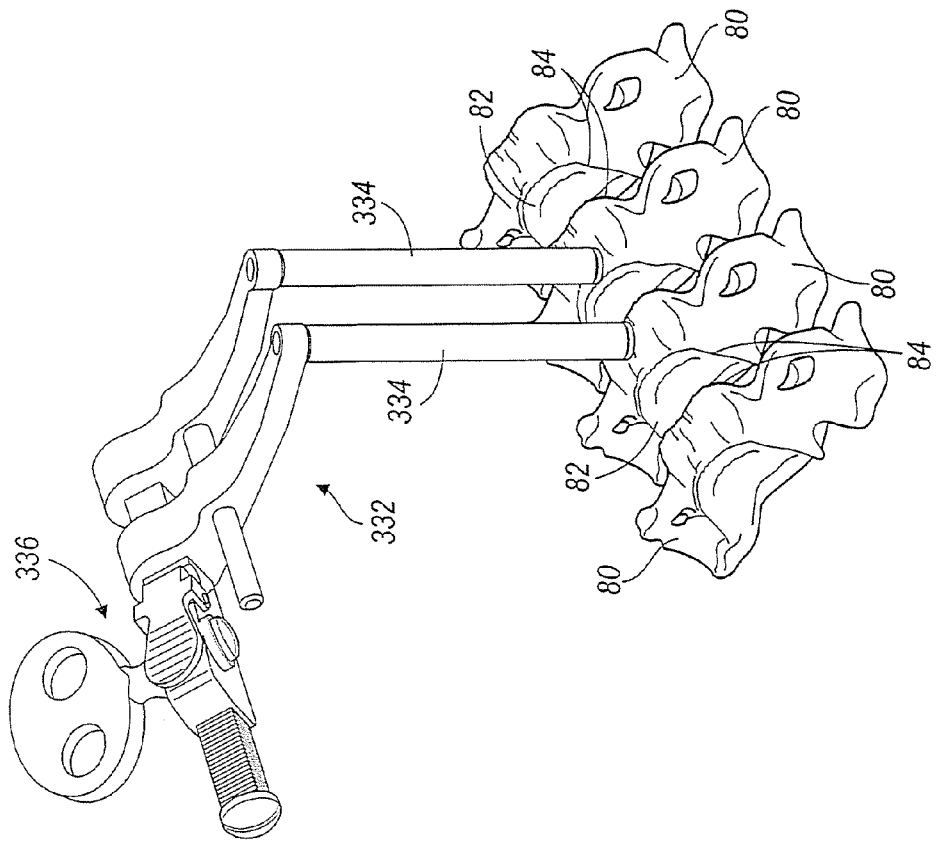

Referring to FIGS. 21-30, a distractor 332 can be used for facilitating the implantation procedure. The distractor 332 can include a pair of tubular legs 334 and a distraction mechanism 336 for applying and controlling the amount of distraction, if any, desired by the surgeon. The distractor legs 334 can be placed over the pins 330, as illustrated in FIG. 21. The depth of inferior vertebral body can be measured using a depth gauge, such as the fossa locator 206 illustrated in of FIG. 8. This measurement can be used to determine the drilling depth.

Figure 24:
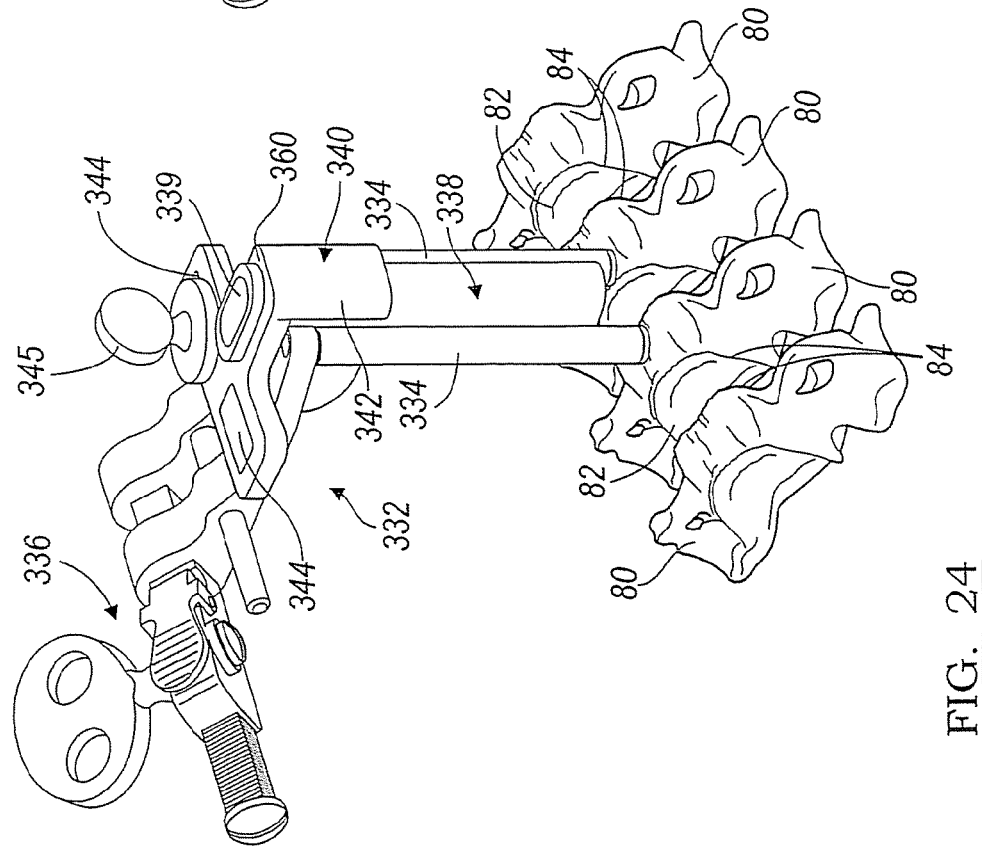

Referring to FIGS. 22-27 and 34, the centering shaft 320 can be inserted into the disc space. A drill guide cannula 338 can be positioned over the centering shaft 320 and between the legs 334 of the distractor 332. The drill guide cannula 338 can be secured on the distractor 332 with a cannula lock 340. The cannula lock 340 can include a longitudinal element 342 defining a first opening 361 configured for receiving the drill guide cannula 338 therethrough, and a flange 360 at an angle to the longitudinal element 342. The flange 360 can define one or more flange openings 344 for engaging a locking element 345, such as a thumb screw. The drill cannula 338 can be pre-assembled in the cannula lock 340 through the first opening 361, and the assembly can be placed over the centering shaft 320. The flange 360 of the cannula lock 340 can sit on the distractor 332, and the drill guide cannula 338 can be secured on the distractor 332 by tightening the locking element 345 through one of the flange openings 344. The drilling depth can be measured by reading markings provided on the centering shaft 320 at the top of the drill guide cannula 338, as described above in connection with the fossa locator 240 illustrated in FIG. 8, and compared with the required drilling depth determined earlier. After the drilling depth is confirmed, the centering shaft 320 can be removed, as shown in FIG. 24.

Figure 34:
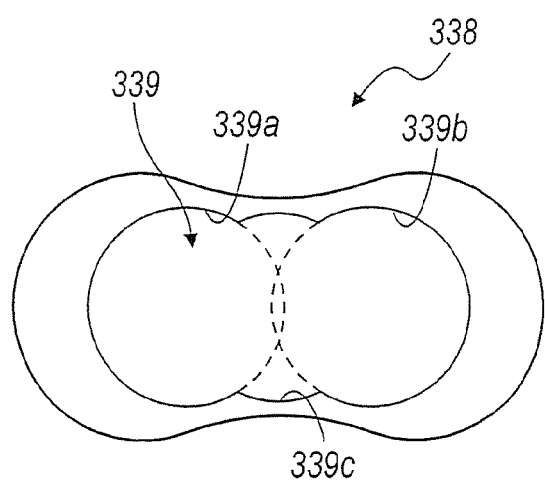
FIG. 34 is a sectional view of a cutting tool guide cannula according to the present teachings.
Figure 35:
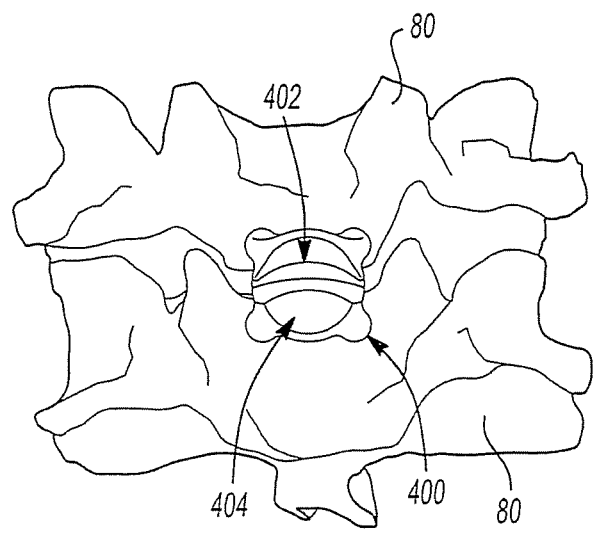
FIG. 35 is a frontal view of an intervertebral implant according to the present teachings, shown implanted in a spine.

Referring to FIGS. 25-27 and 34, the drill guide cannula 338 can include a longitudinal opening 339 adapted for receiving the centering shaft 320 for locating guidance, and other instruments, such as a drill 346 which can be inserted in more than one position relative to the longitudinal opening 339, as appropriate for preparing the disc space for accommodating the overall geometry of the particular intervertebral implant 100. For example, for the bi-cylindrical intervertebral implant 100 illustrated in FIGS. 1A, and 17A-17C, the drill 346 can be positioned in first and second positions defined by first and second open intersecting circles 339a, 339b of the longitudinal opening 339 of the drill guide cannula 338, as illustrated in FIG. 34, and corresponding to the circles 309a, 309b of the bi-cylindrical intervertebral implant 100 illustrated in FIG. 17B. The centering shaft 320 can be received in an intermediate position defined by a third circle 339c of smaller diameter than the first and second circles 339a, 339b, and intersecting the first and second circles 339a, 339b, as illustrated in FIG. 34.

Figure 27:
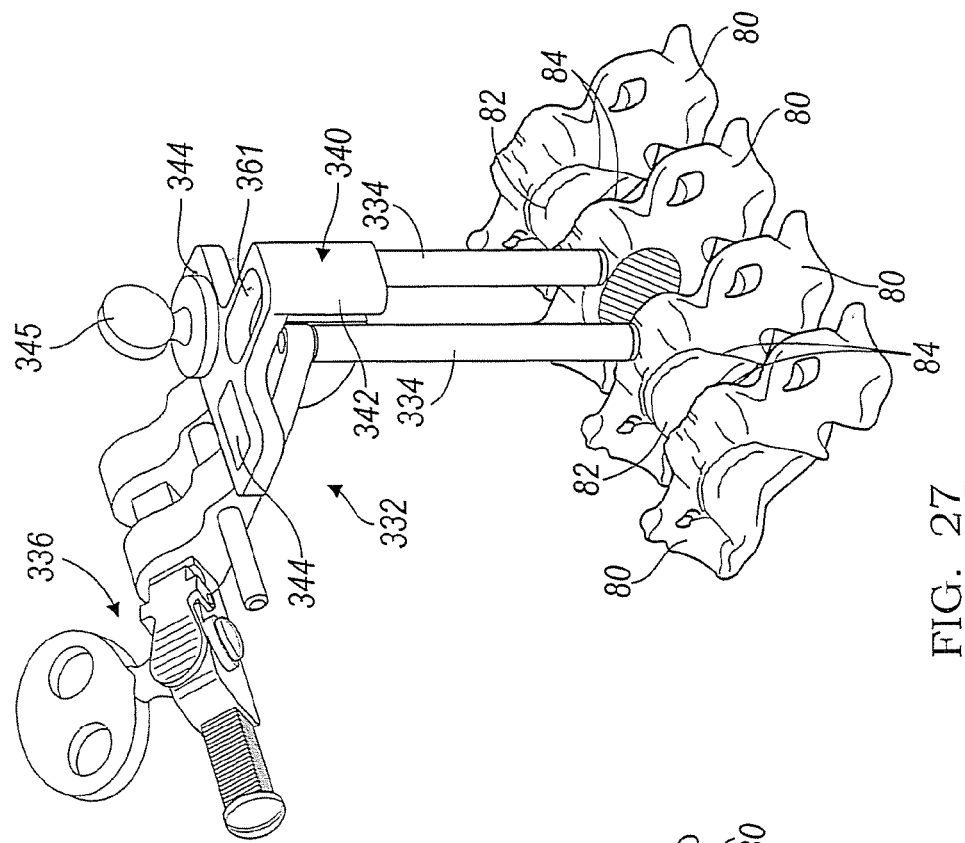
Figure 26:
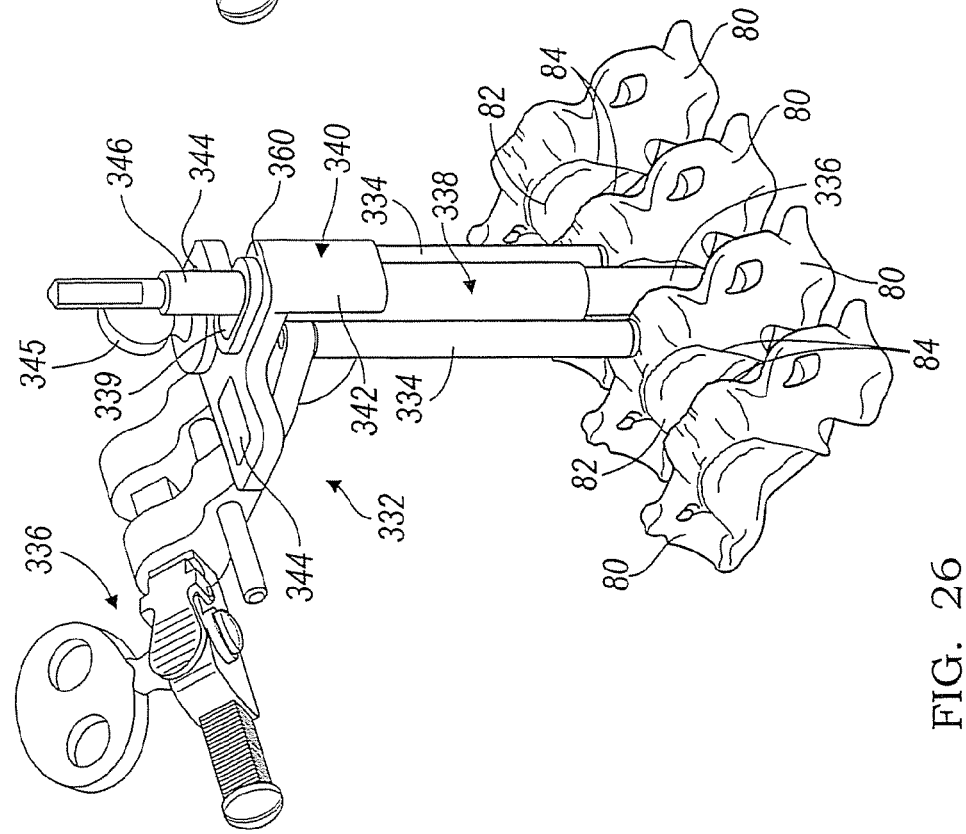
Figure 29:
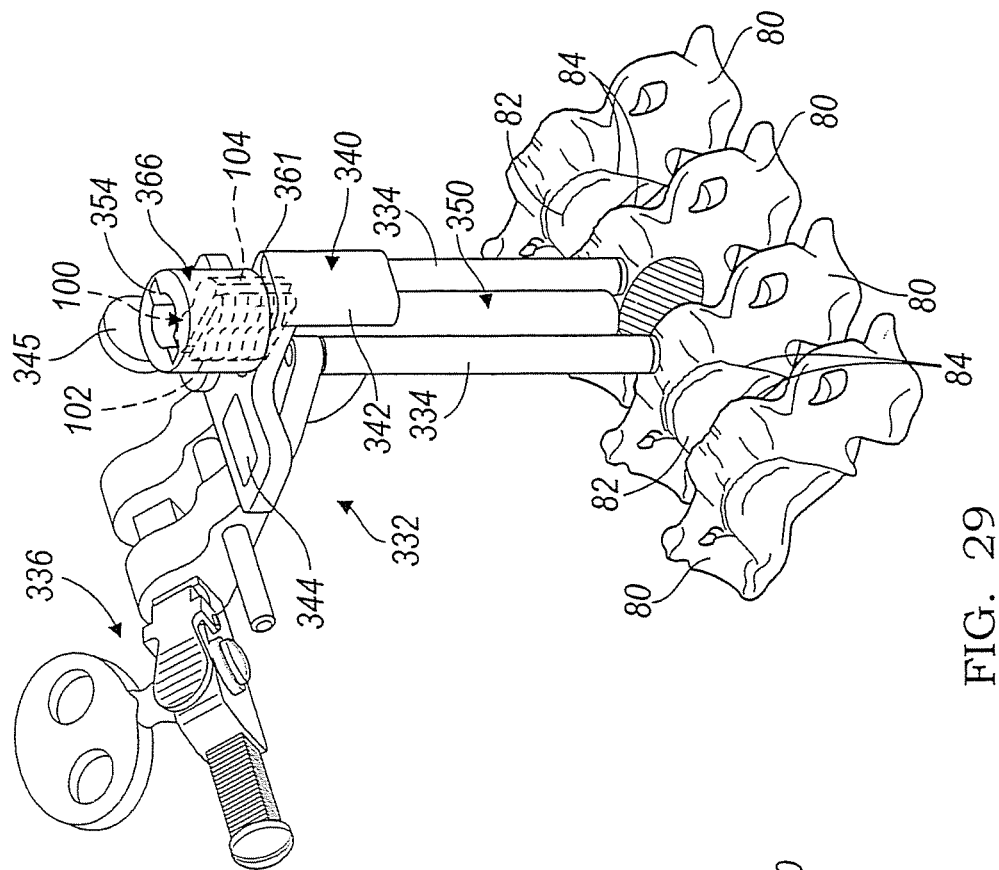
Figure 28:
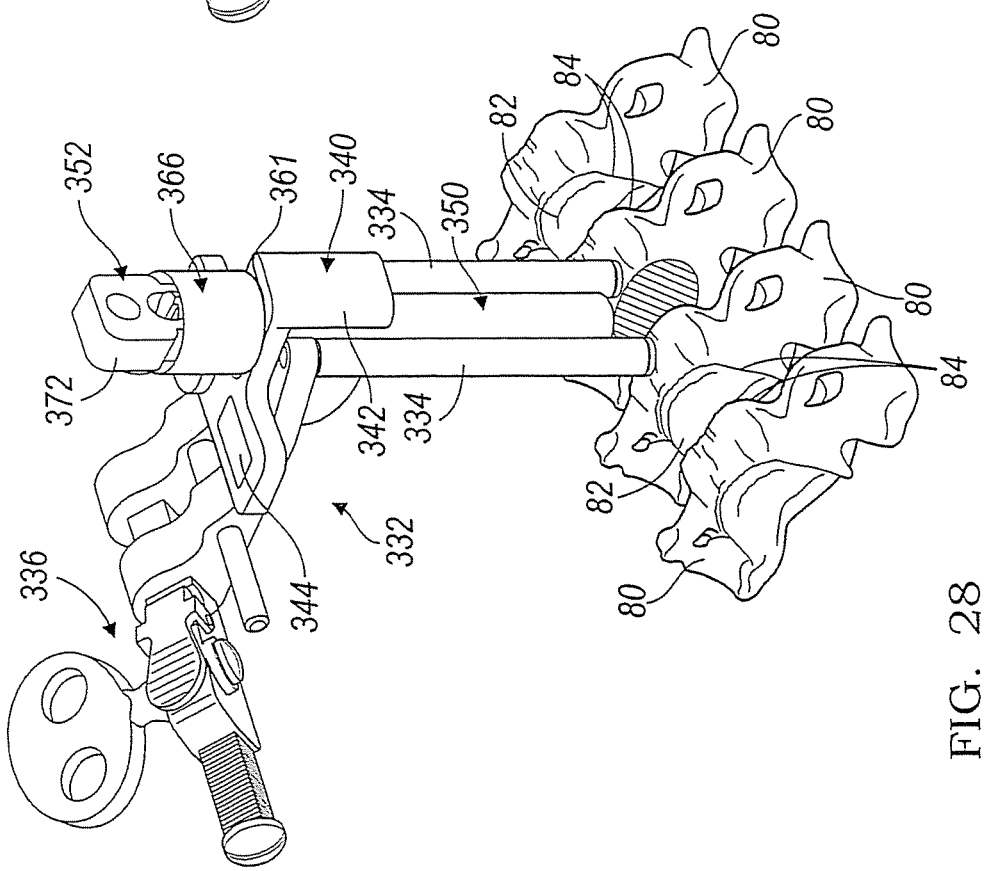

In one exemplary embodiment, flat-bottomed holes having diameter of about 8 mm can be drilled to a depth determined as described above. Drill stops can be used to control the depth of drilling and/or broaching. The desired depth can align the center of the intervertebral implant 100 with the nuclear recess 86. After drilling, bone debris can be removed by irrigation and suction, and the drill guide cannula 338 can be pulled out of cannula lock 340 and completely removed, as illustrated in FIG. 27. The drill guide cannula 338 can be sized such that it stops short of the vertebrae defining a gap 362 between the distal end of the cannula 338 and the vertebrae, as can be seen in FIG. 26. The gap 362 can facilitate the removal of the drill guide cannula 338 after drilling.

Figure 30:
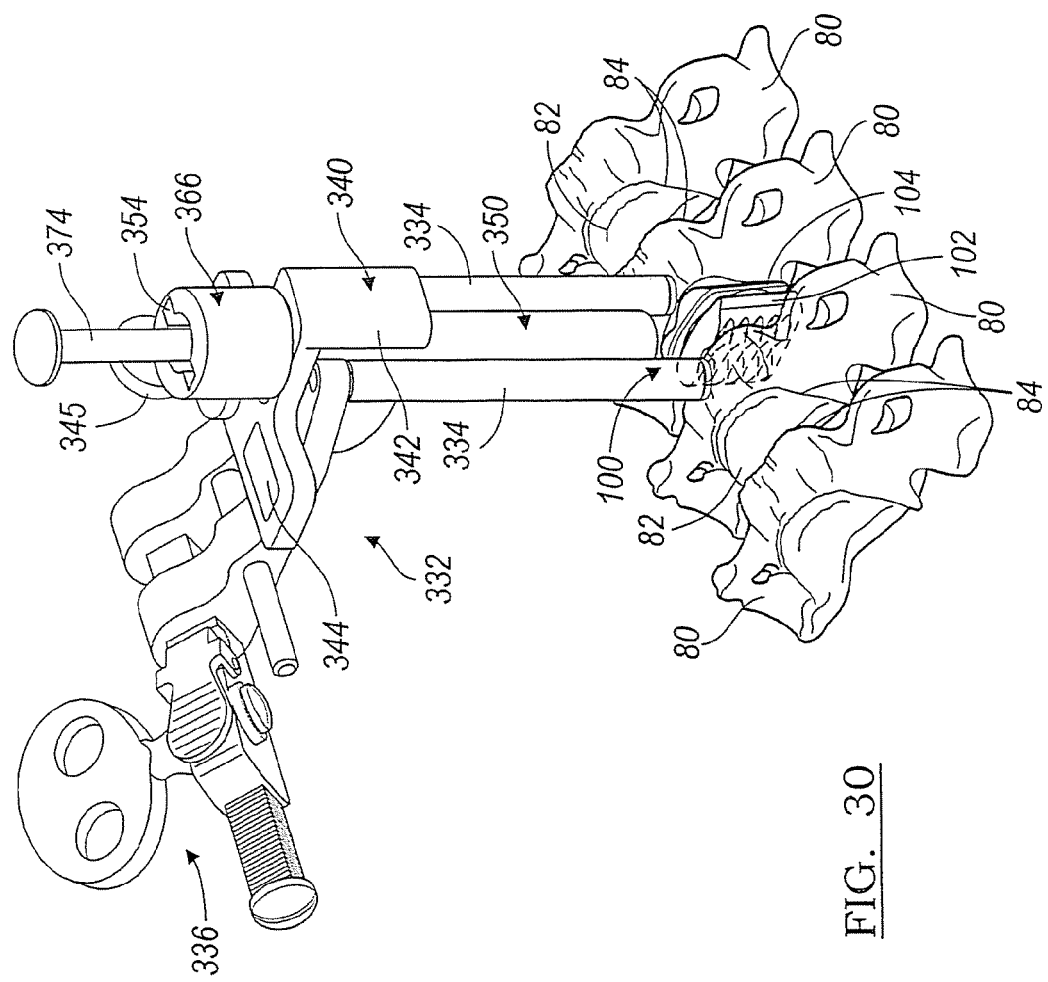
Figure 31:
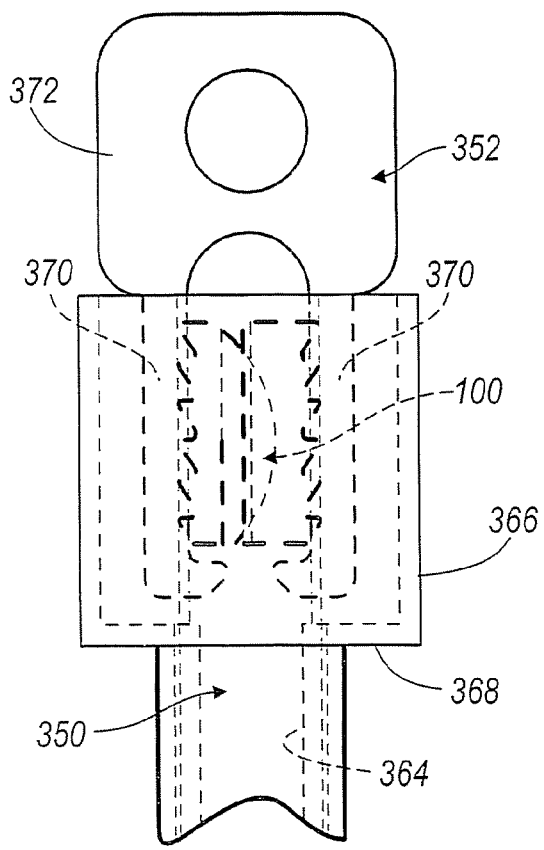
FIG. 31 is a side view of a clip holding an intervertebral implant in an insertion cannula according to the present teachings.
Figure 32:
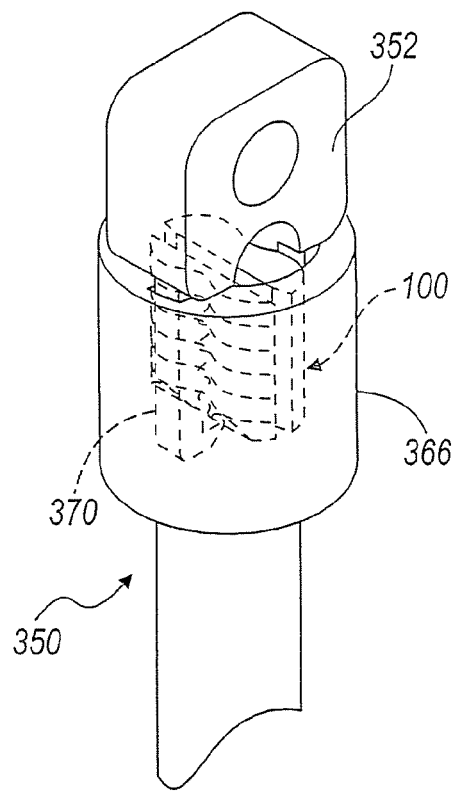
FIG. 32 is a view of a clip holding an intervertebral implant in an insertion cannula according to the present teachings.

Referring to FIGS. 28-32, an elongated insertion cannula 350 can be inserted into the first opening 361 of the cannula lock 340. The insertion cannula 350 can be pre-loaded with the intervertebral implant 100, as illustrated in FIGS. 31 and 32. The insertion cannula 350 can be made of smooth plastic that can protect the intervertebral implant 100 from scratching, for example, and can be disposable. The insertion cannula 350 can include a longitudinal bore 364. The longitudinal bore 364 can be shaped to conform to, and/or otherwise accommodate the shape of the intervertebral implant 100, for example the bi-cylindrical intervertebral implant 100, as illustrated in FIG. 31. The shape of the longitudinal bore 364 can also maintain the relative position of the components 102, 104 of the multiple-component intervertebral implant 100. The insertion cannula 350 can include an enlarged tubular proximal end 366, which can provide a shoulder 368 resting on the cannula lock 340 when the insertion cannula 350 is inserted through the first opening 361 of the cannula lock 340.

Referring to FIGS. 28-32, the intervertebral implant 100 can be held in the enlarged proximal end 366 of the insertion cannula 350 using a removable retainer or other temporarily retaining device, such as a clip 352, for example. The clip 352 can hold the intervertebral implant 100 at a substantially fixed position within the longitudinal bore 364 of the insertion cannula 350, and maintain the relative positions of the superior and inferior components 102, 104 of the intervertebral implant 100. The clip 352 can be substantially flat and can include a head 372 and two compliant arms 370 extending from the head 372. The compliant arms 370 that can hold the intervertebral implant 100 at the concave intermediate portions 304, 310 of the intervertebral implant 100 shown in FIG. 17B. The arms 370 can be received through a diametrical slot 354 of the proximal end 366 of the insertion cannula 350, or other appropriate opening thereon. The clip 352 can be inserted from the proximal end 366 of the insertion cannula 350, and can be removed by pulling out the proximal end 366. Removing the clip 352 causes the arms 370 to open, thereby releasing the intervertebral implant 100 into the bore 364 of the insertion cannula 350. A plastic tamp 374 can be used to push the intervertebral implant 100 through the insertion cannula 350 and into the prepared disc space, as illustrated in FIG. 30. The insertion cannula 350, the distractor 332 and the distraction pins 330 can then be removed leaving the intervertebral implant 100 appropriately positioned, as illustrated in FIG. 1A.

The intervertebral implant 100 can be provided in a sterilized kit that includes the insertion cannula 350. The intervertebral implant 100 can be preloaded in the insertion cannula 350 and held by the clip 352. The tamp 374 can also be included in the kit. Kits including intervertebral implants 100 of different sizes can be provided. After use, any of the insertion cannula 350, the clip 352 and the tamp 374 can be disposed, or re-sterilized and re-used.

Figure 10:
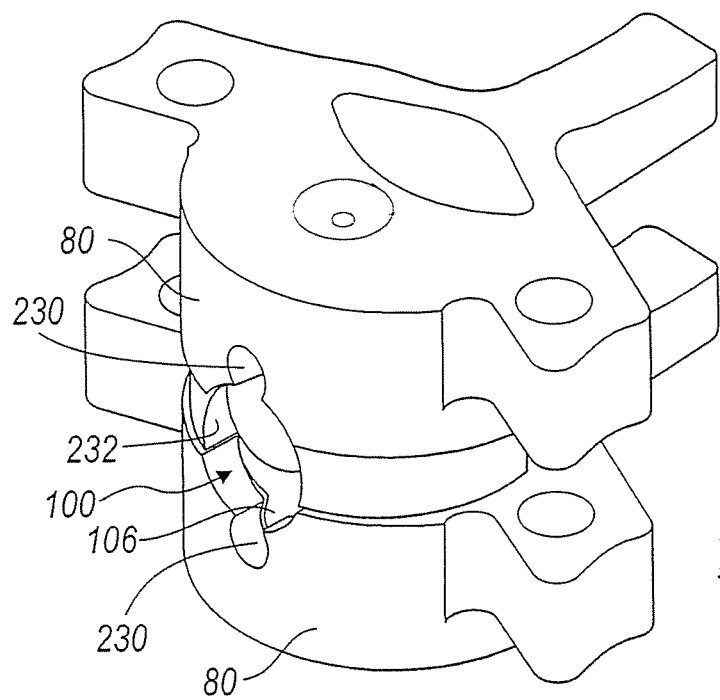
FIG. 10 is an isometric view of an intervertebral implant according to the present teachings, shown implanted.
Figure 11:
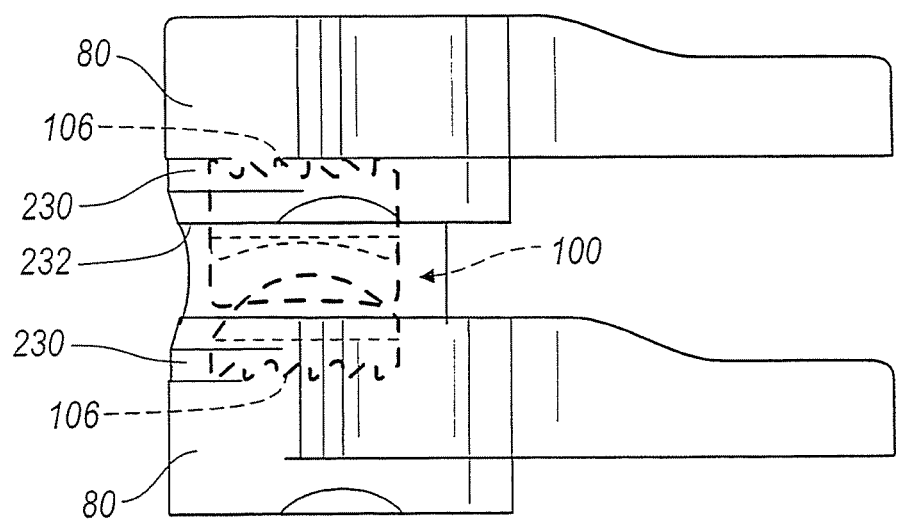
FIG. 11 is a sagittal sectional view of the intervertebral implant of FIG. 10.
Figure 13A:
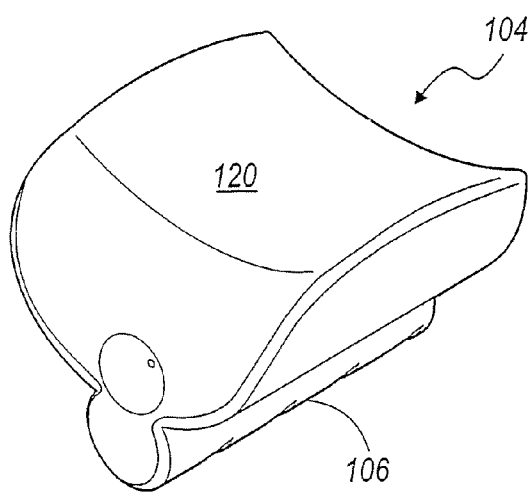
FIG. 13A is an isometric view of an inferior component of a toroidal intervertebral implant according to the present teachings.
Figure 13B:
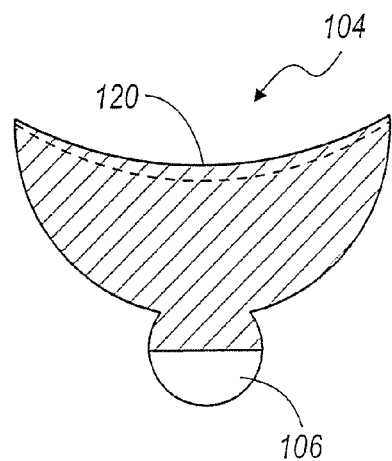
FIG. 13B is a coronal sectional view of the inferior component of the toroidal intervertebral implant of FIG. 13A.
Figure 13C:
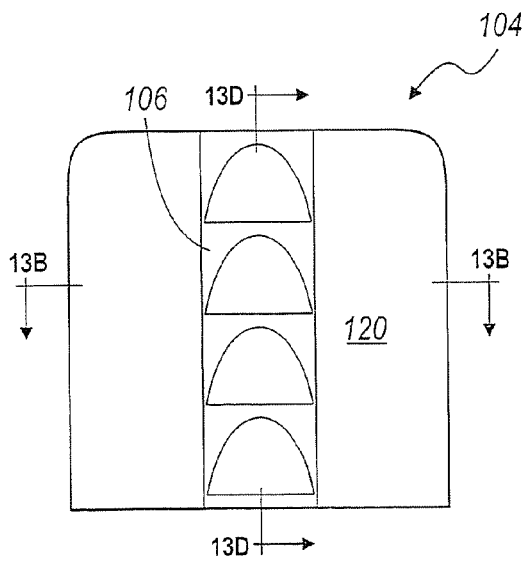
FIG. 13C is an axial view of the inferior component of the toroidal intervertebral implant of FIG. 12A.
Figure 13D:
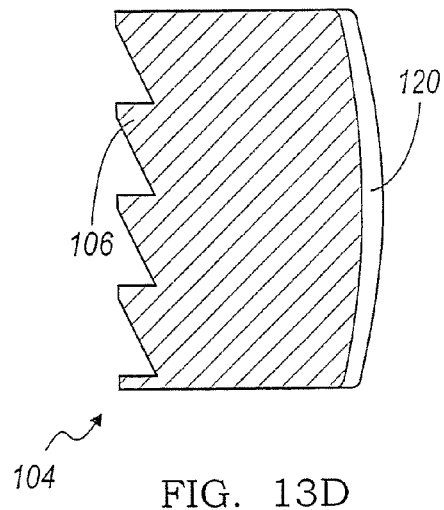
FIG. 13D is a sagittal sectional view of the inferior component of the toroidal intervertebral implant of FIG. 13A.

Although the method of implanting the intervertebral implant 100 and associated instruments was described above in reference to the bi-cylindrical intervertebral implant 100 illustrated in FIGS. 17A-17C, similar procedures can be used for implanting the toroidal and spherical intervertebral implants 100 illustrated in FIGS. 2, 4 and 6. Referring to FIGS. 10 and 11, for example, a pair of holes 230 can be drilled to the required depth as determined by the graduated markings 220 of the fossa locator 206 for accommodating the serrated racks 106 of the toroidal or spherical intervertebral implant 100. A central hole 232 can be drilled per the required depth to accommodate the body of toroidal or spherical intervertebral implant 100. Similarly, the shape of the various implantation instruments, such as the drill guide cannula and the insertion cannula, for example, can be designed to accommodate the toroidal or spherical implant.

Referring to FIGS. 35-49, instruments and methods for implanting an intervertebral implant 400 according to the present teachings are illustrated. The intervertebral implant 400 illustrated in FIGS. 35-40, similarly to the intervertebral implant 100 described above, can include superior and inferior articulation components 402, 404 with corresponding superior and inferior articulating surfaces 401, 403. The articulation surfaces 401, 403 can provide articulation of the spherical or toroidal type, which was described above in connection with the intervertebral implant 100 and will not be repeated here. The superior and inferior articulating components 402, 404 can include respective superior and inferior bone engagement surfaces 405, 409 having bone engagement formations defined by alternating and smoothly curved crests 412 and grooves 414, or other geometry corresponding to keels, pegs, or other endplate engagement structures. It will be understood that the implant 100 can be a multiple-component implant and that each of the superior and inferior articulation components 402, 404 can be modular including separate endplate engagement and articulation portions as discussed in connection to the implant 100 shown in FIGS. 6 and 7.

Figure 36:
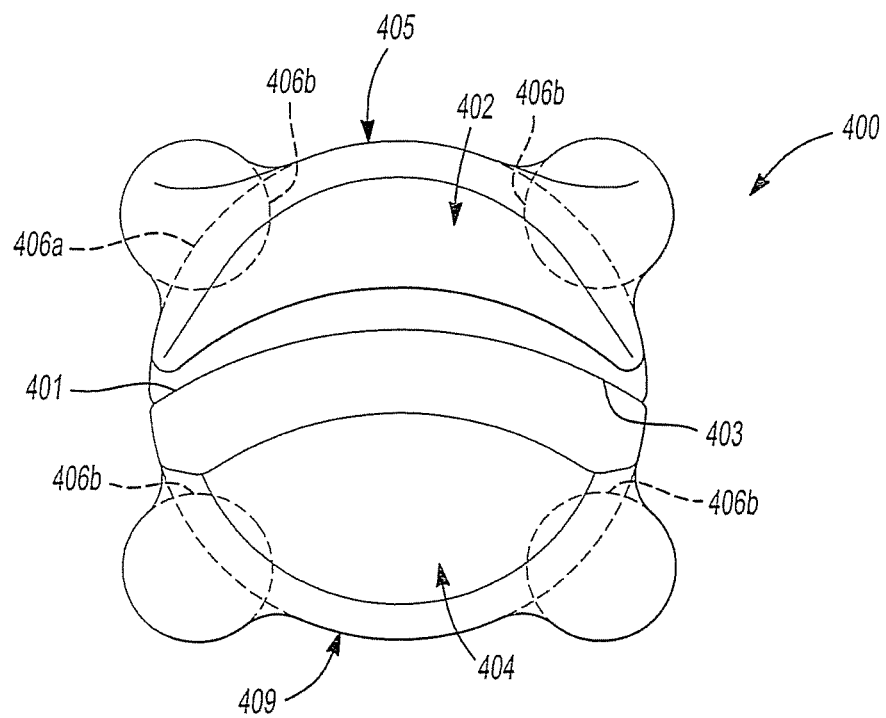
FIG. 36 is a frontal view of an intervertebral implant according to the present teachings.
Figure 37:
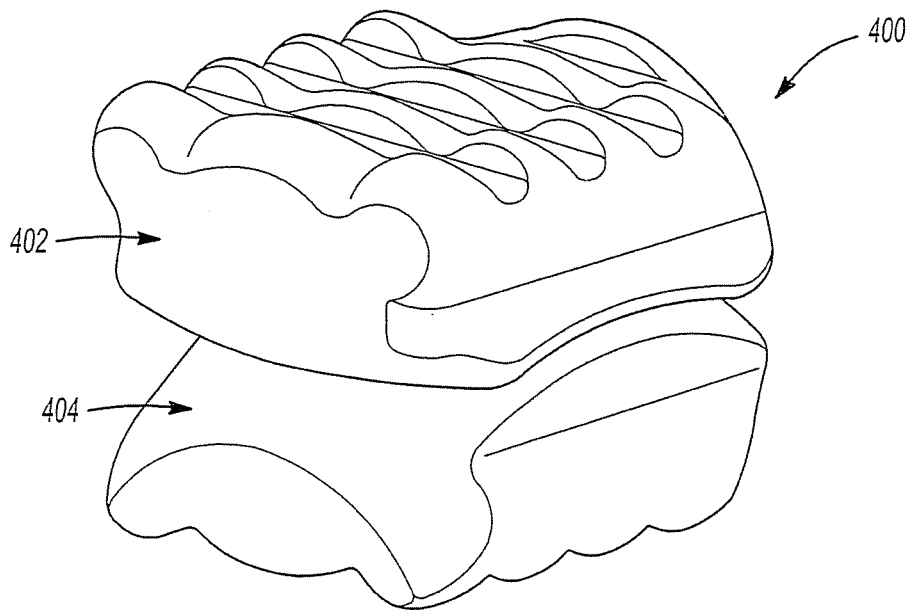
FIG. 37 is an isometric view of the implant of FIG. 36.
Figure 38:
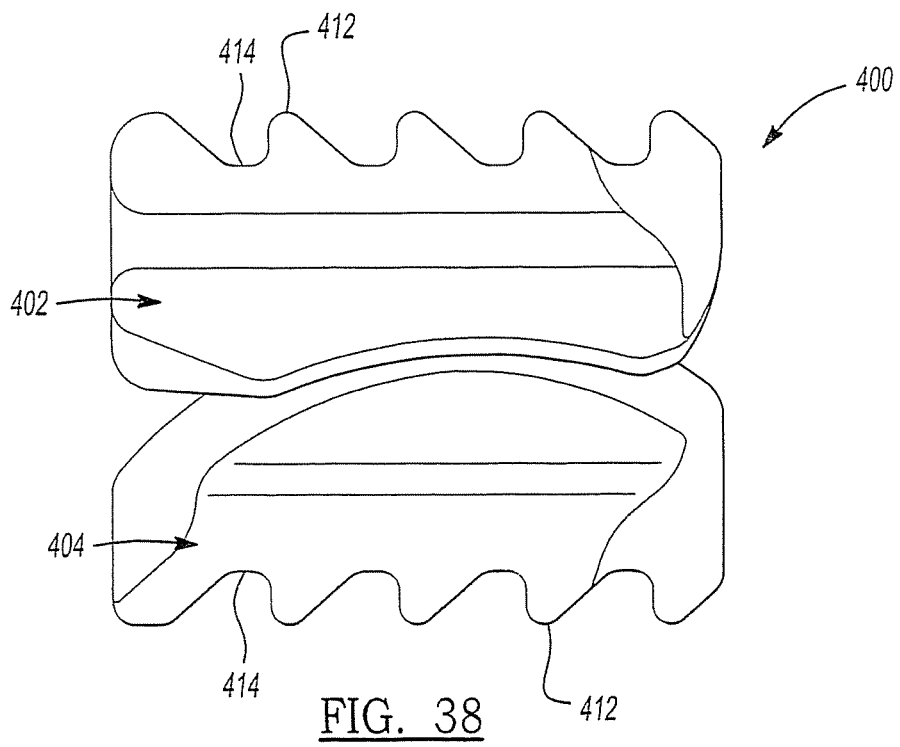
FIG. 38 is a side view of the implant of FIG. 36.
Figure 39:
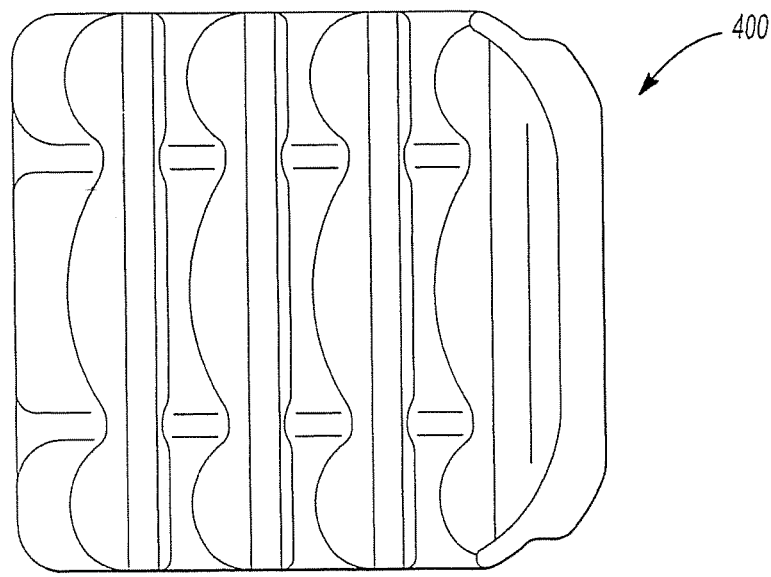
FIG. 39 is a top view of the implant of FIG. 36.
Figure 40:
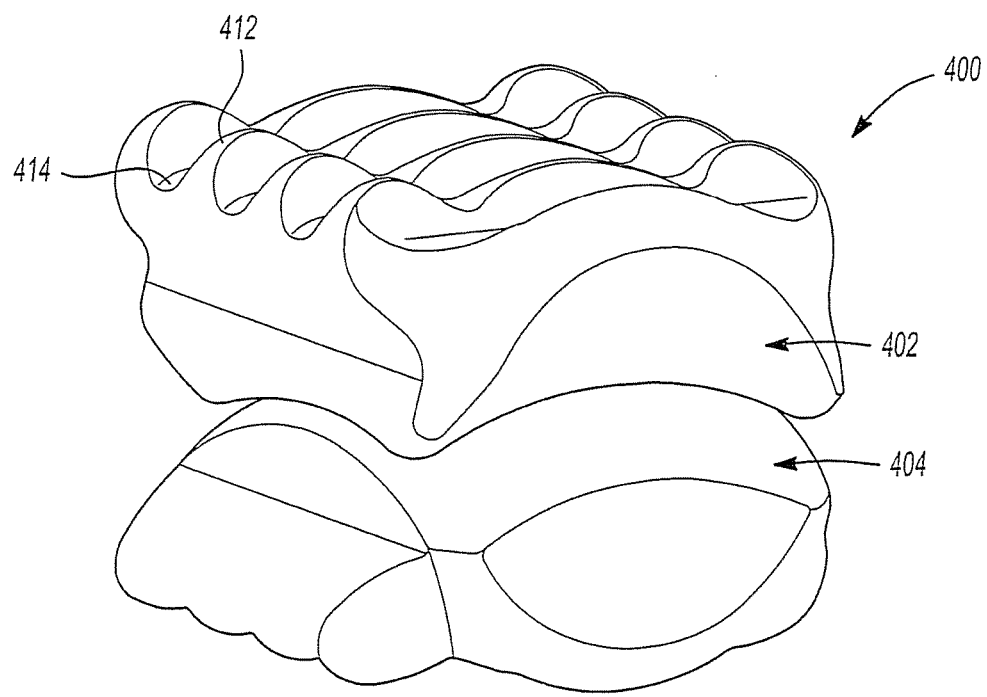
FIG. 40 is another isometric view of the implant of FIG. 36.

The curved outer surface of the intervertebral implant can be defined as the envelope of five intersecting cylinders including a central cylinder 406a and four smaller corner cylinders 406b, as shown in FIG. 36. The five cylinders 406a, 406b can all have circular cross-sections. Non-intersecting cylinders can also be used as well. Accordingly, each of the superior and inferior bone engagement surfaces 405, 409 can include three cylindrical portions defined by the outer portions of cylinders 406a and 406b.

An exemplary method of implanting the intervertebral implant 400 and the associated instruments is described with particular reference to FIGS. 41-49. Preparatory to implantation, a complete discectomy can be performed, including removal of any overhanging osteophytes. The depth of the vertebral bodies 80 can be measured using a conventional depth gauge for determining the depth of insertion of the implant 400, or by any other method known in the art.

Figure 41:
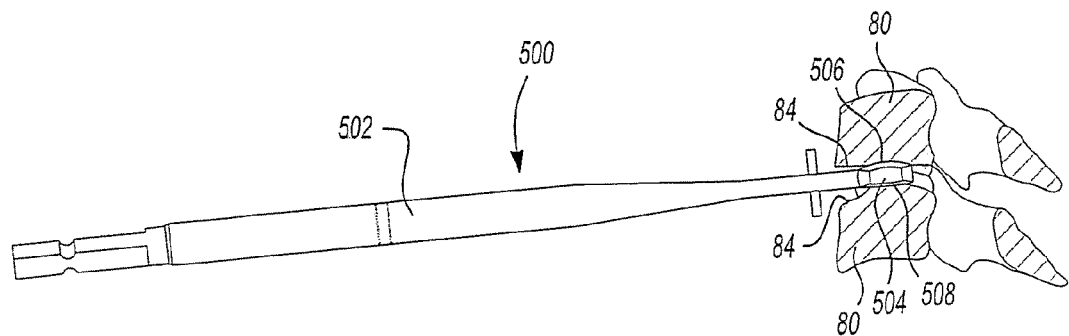
FIG. 41 is an environmental view of a disc sizer according to the present teachings.
Figure 42:
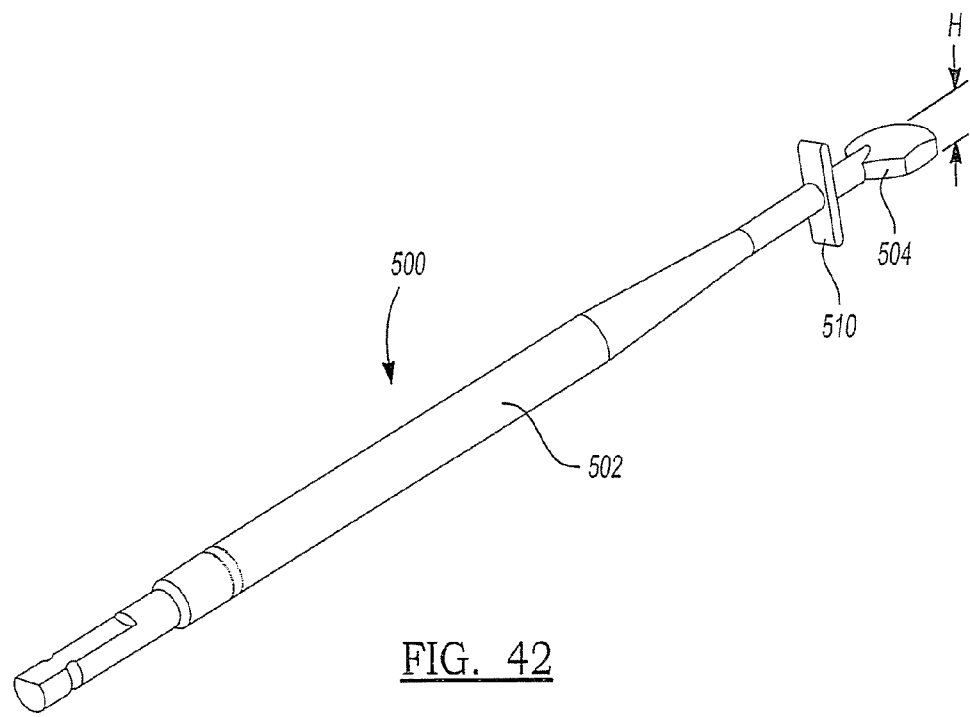
FIG. 42 is an isometric view of the disc sizer of FIG. 41.

Referring to FIGS. 41 and 42, a series of disc-sizers 500 of different heights can be used to evaluate the height of the disc space. An exemplary disc sizer 500 can have an elongated shaft 502 and a distal plate-like tip 504 that can have a convex superior surface 506 and a substantially but not completely flat inferior surface 508 defining having a maximum distance or height "H" therebetween. The shape of the distal tip 504 can mate to the natural surfaces of the endplates 84 such that the highest portion of the disc space at the center of the nuclear recess can be measured. The operating surgeon can first try a small disc sizer 500 having a distal tip 504 of small height H, and then sequentially use disc sizers 500 with increasing height H until a close fit can be achieved. The disc sizer 500 can include a plate-like stop member 510 at a predetermined distance from the distal tip 504 and substantially perpendicular to the shaft 502 of the disc sizer 520. The stop member 510 can prevent the disc sizer 500 from going too deeply and injuring the spinal cord, if a too-small disc sizer is used. The stop member 510 can also be adjustable.

Figure 43:
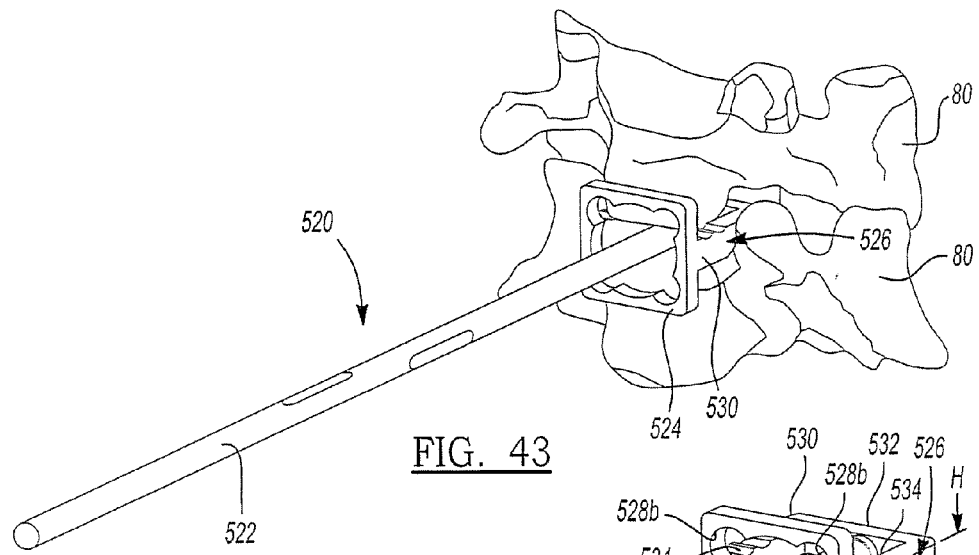
FIG. 43 is an environmental view of a spacer guide according to the present teachings.
Figure 44:
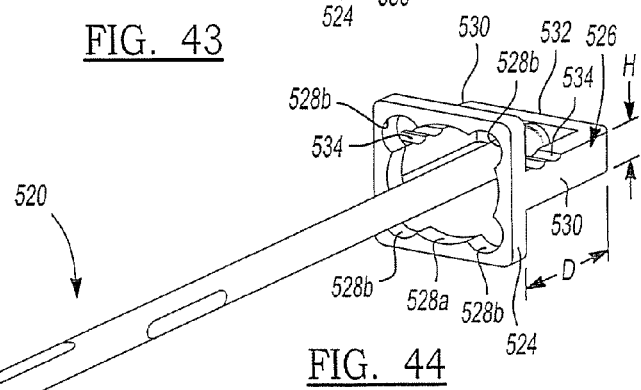
FIG. 44 is an isometric view of the spacer guide of FIG. 43.

Referring to FIGS. 43 and 44, an appropriately sized spacer guide 520 can be inserted into the disc space. The spacer guide 520 can be used as a starting base for making a central hole and four corner holes corresponding to the five cylinders 406a, 406b that define geometry of the implant 400. The depth of insertion "D" of the spacer guide 520 corresponds to the depth determined by the depth gauge, and the thickness/height "H" correlates to the size determined by the disc sizer 500, as described above. The spacer guide 520 can include an elongated shaft 522 over which various cannulated drills can be placed to prepare the endplates 84 for receiving the implant 400, as discussed below. The spacer guide 520 can include a depth stop flange 524 substantially perpendicular to the shaft 522. The flange 524 can abut against the anterior face of the vertebral bodies 80 to stop the spacer guide 520 at the appropriate depth D. The flange 524 can have a central cutout 528a and four smaller tool-guiding cutouts 528b at the four corners for allowing passage of drills or other cutting tools that can be used to prepare the endplates 84 for receiving the implant 400. For example, the four corner cutouts 528b can receive drills for making holes corresponding to the cylinders 406b of the implant 400, shown in FIG. 36. The central cutout 528a can receive a drill for making a central hole corresponding to the central cylinder 406a of the implant 400. Accordingly, the periphery defined by the cutouts 528a, 528b, generally or collectively referenced as cutouts 528, can correlate to the size and outer shape of the implant 400 for guiding various cutting tools that prepare the vertebral endplates 84 for receiving the intervertebral implant 400. It will be appreciated that the spacer guide 520 can be similarly used with other instruments for cutting bone in addition to drills, such as, for example, reamers, rasps, punches and chisels. Further, the spacer guide 520 need not be limited for use with the particular geometry of the intervertebral implant 400, but can also be used for other implant geometries, such as, for example, the implants identified by reference numbers 100 hereinabove. Accordingly, the flange 524 can have tool-guiding cutouts 528a/528b of different shapes and locations along the flange 524 for guiding instruments corresponding to keels, pegs and other anchoring devices of the implant. For the implant 100 shown in FIG. 4, for example, the flange 524 can have two central cutouts corresponding to the racks 106 or other keels or pegs for engaging the endplates 84 of the vertebral bodies 80. Similarly, the flange 524 can include cutouts 528 corresponding to the engagement formations 312 of the implant 100 shown in FIG. 17A.

The spacer guide 520 can also include a depth stop frame member 526 that can extend into the disc space and can also serve as a hard stop for the drills. The frame member 526 can have a substantially planar U-shape that extends from the flange 524 to the distal end of the shaft 522. The frame member 526 can also be tapered for ease of insertion. The frame member 526 can be substantially perpendicular the flange 524 and can have height H, as shown in FIG. 44. The frame member 526 can include two arms 530 connected with distal member 532 that provides a stop for drills. The angle defined by the distal member 532 and each of the arms 530 can be chamfered or tapered or rounded, and can also be less than 90 degrees. The distal member 523 can also have a tapered or angled cross-section for facilitating insertion. The arms 530 can be parallel or can be inclined defining a tapering providing for lordosis. The arms 530 of the frame member 526 can have serrations or teeth or other texturing on the arm surfaces that contact the inferior and superior surfaces of the vertebral bodies 80 to help stabilize the spacer guide 520 in the disc space. The spacer guide 520 can be made in many sizes that provide a variety of heights H for each depth D and size of implant combination such that a snug fit can be achieved in the disc space.

Figure 45:
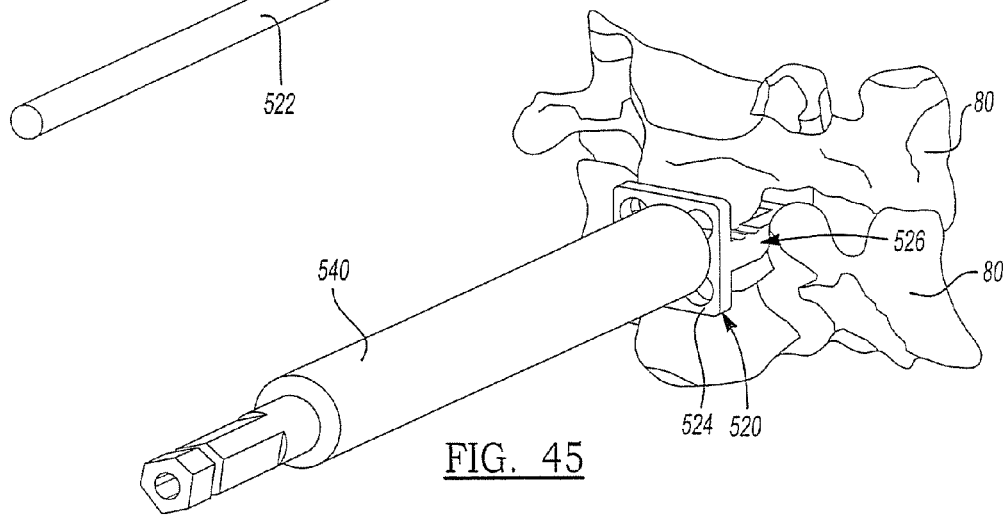
FIG. 45 is an environmental isometric view illustrating drilling a central hole for the implant according to the present teachings.

Referring to FIG. 45, a cannulated drill 540 can be placed over the shaft 522 of the spacer guide 520 to prepare a center hole that corresponds to the diameter of the central cylinder 406a of the implant 400. A series of different diameter drills 540 of sequentially increasing diameters can be used until the final diameter is reached. Bone debris from drilling can be removed by irrigation and suction, as well as by the geometry of the cutting instruments.

Figure 46:
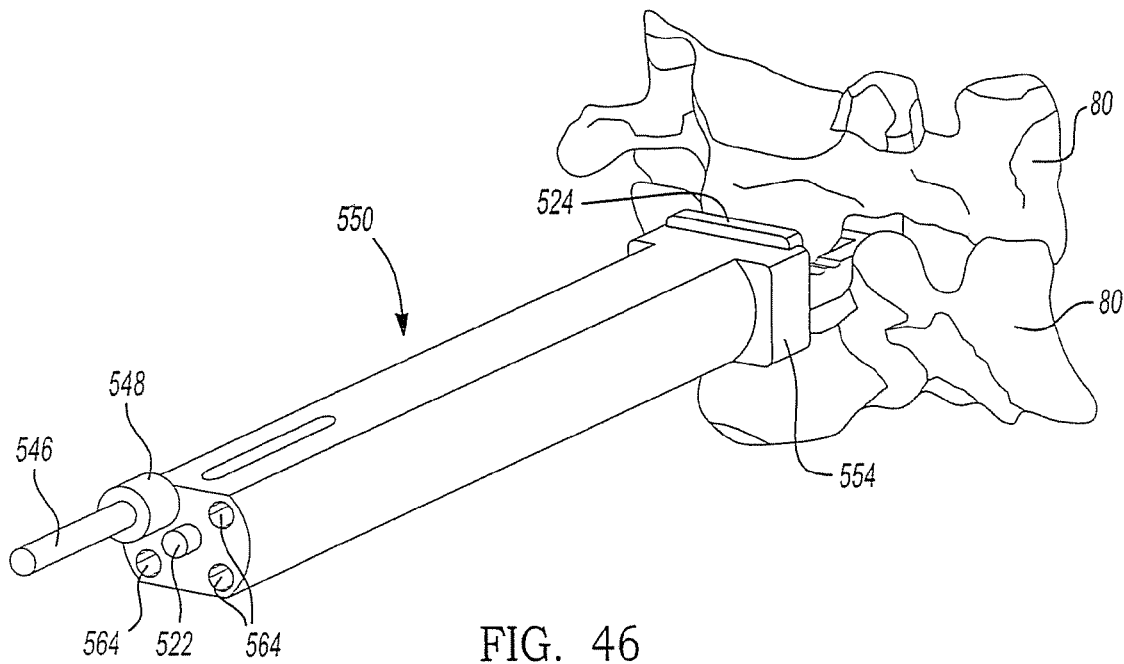
FIG. 46 is an environmental isometric view illustrating drilling four holes for the implant according to the present teachings.
Figure 47:
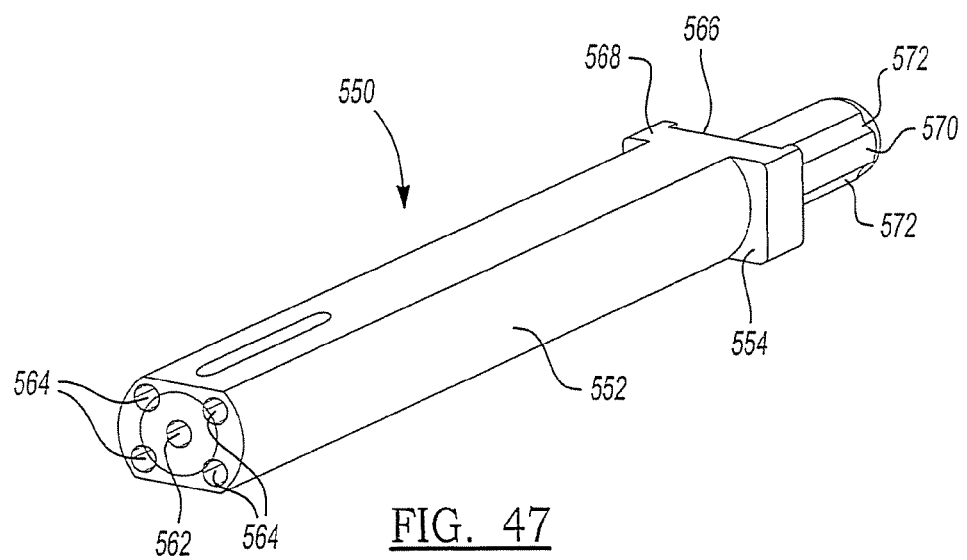
FIG. 47 is an isometric view of a drilling guide according to the present teachings.

Referring to FIGS. 46 and 47, a cutting tool guide 550 for the corner holes can be placed over the spacer guide 520. The cutting tool guide 550 can include a body 552, a distal flange 554 and a boss 570 extending beyond the distal flange 554. The cutting tool guide 550 can be cannulated, defining a central longitudinal bore 562 that can receive the shaft 522 of the spacer guide 520. The cutting tool guide 550 can also include four longitudinal corner bores or other guiding bores 564 that can receive respective drills 546 for drilling four holes corresponding to the corner cylinders 406b of the implant 400. The guiding bores 564 can be offset from the central longitudinal bore 562 in a direction transverse to the central longitudinal bore 562. It will be appreciated that the number and location of the guiding bores 564 can vary depending on the need to create slots for pegs, keels or other engagement formations of the implant 400 or 100 with the endplates, as discussed above in connection with the spacer guide 520. The distal flange 554 can include two projections 568 defining a holding slot 566 for holding the flange 524 of the spacer guide 520 and preventing rotation of the cutting tool guide 550 relative to the spacer guide 520.

When the cutting tool guide 550 is placed over the spacer guide 520, the boss 570 extends along the frame member 526 of the spacer guide 520 and into the disc space prepared by drilling the central hole with the cannulated drills 540. The boss 570 can be substantially the same size as the central hole or smaller. The boss 570 can include guiding grooves 572 aligned with the corresponding corner bores 564 for guiding the drills 546 to drill straight holes into the endplates 84 of vertebral bodies 80. The same drill 546 can be used sequentially to drill all four holes, or alternatively each hole can be drilled with a new drill bit and the old drill 546 left in the cutting tool guide 550 for stability during the remainder of the drilling. The drill 546 can include a stop 548 that can contact the cutting tool guide 550 to stop the drill 546 at the appropriate depth. The distal member 532 of the spacer guide 520 can provide a stop for the drills used for the smaller corner holes. Bone debris can be removed by irrigation and suction. It will be appreciated that the shape and location of the guiding grooves 572 can vary according to the geometry of the implant, as discussed above in connection with the guiding bores 564.

Figure 48:
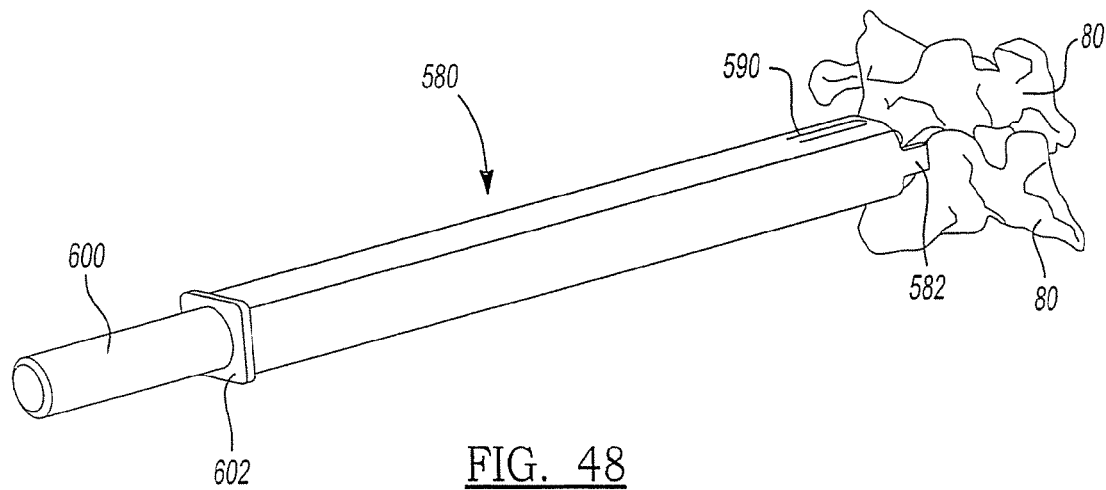
FIG. 48 is an environmental isometric view illustrating inserting an implant according to the present teachings.
Figure 49:
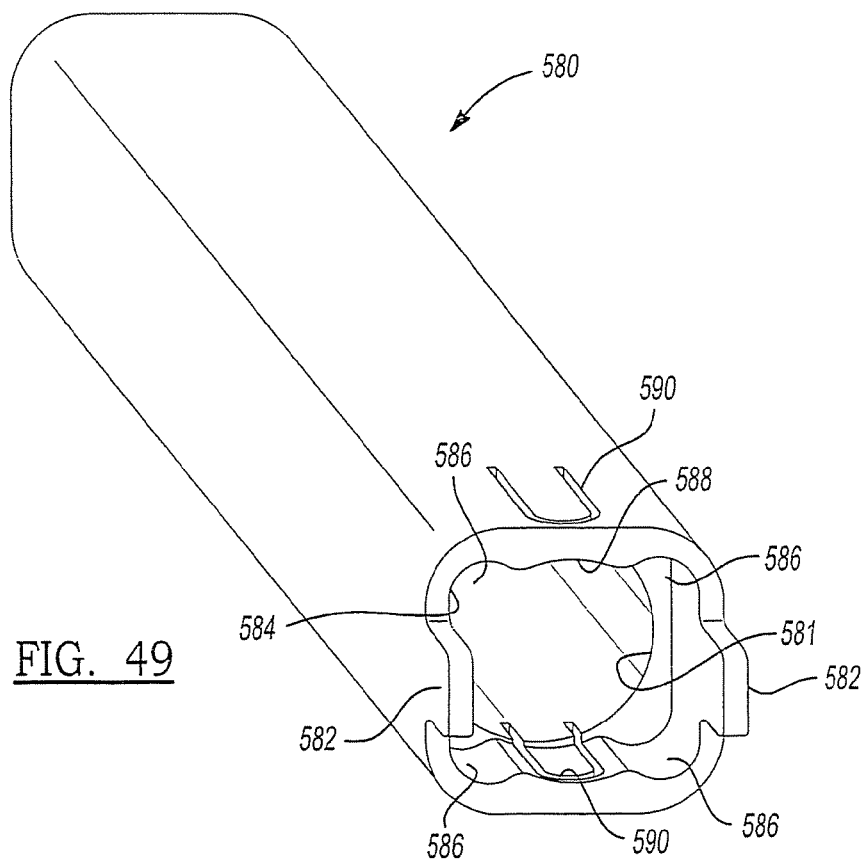
FIG. 49 is an isometric view of an insertion cannula according to the present teachings.

After the four holes corresponding to four cylinders 406b of the implant 400 have been drilled, the spacer guide 520, the cutting tool guide 550 and drills 546 can be removed from the prepared disc space. Referring to FIGS. 48 and 50, an insertion cannula 580 pre-loaded with the implant 400 and a tamp or pusher member 600 can be used to insert the implant 400 into the prepared disc space. Alternatively, the insertion cannula 580 can be loaded intraoperatively. The insertion cannula 580 can also have markings for alignment. The insertion cannula 580 can include a bore 581 that can receive the tamp member 600. The cannula 580 can include a retainer or clip defined by two compliant arms 590 integrally formed on the distal portion of the insertion cannula 580 for holding the implant 400. The distal portion of the insertion cannula 580 defines a bore portion 584 configured to mate with the implant 400. The bore portion 584 can be defined by five cylindrical surfaces 586 and 588, as shown in FIG. 49 for mating with the five cylinders 406a, 406b of the implant 400. A small portion of the implant 400 can extend out of the bore portion 584 of the insertion cannula 580 for ease in aligning the implant 400 with the prepared disc space. The distal end of the insertion cannula 580 can also include guiding flanges 582 for guiding the implant into the disc space. The distal surface of the insertion cannula 580 excepting the guiding flanges 582 can rest on the anterior faces of the vertebral bodies 80.

The tamp member 600 can be used to slide the implant 400 past the integral clip 588 and into the prepared disc space. The tamp member 600 can also be used to perform final seating of the implant 400 after removal of the insertion cannula 580. The tamp member 600 can have length selected for the desired implantation depth. The tamp member 600 can include a depth stop member 602 that can contact the proximal end of the insertion cannula 580 to indicate that the implant 40 has been fully seated into the prepared disc space.

The method of implanting the intervertebral implant according to the present teachings can be used, at the option of the surgeon, for minimally invasive procedures, using a small incision and removing only as much degenerative material as necessary. Accordingly, a decreased risk of infection, decreased blood loss, decreased exposure to anesthesia and shorter recovery time can be achieved. Further, the methods of the present teachings include relatively few steps and employ simple instrumentation with appropriate hard stops to avoid potential injury to the spinal cord. When instruments of different sizes can be used, those can be color-coded to facilitate selection of the appropriate size. As can be seen from the associated drawings, the instruments have streamlined outlines that allow them to fit easily into the operative site and provide visibility of the vertebral bodies 80 and the surrounding tissues. The vertebral implant is pre-loaded in the insertion cannula, such that assembling and loading the implant during the surgical procedure is avoided.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention.

What is claimed is:

1. An intervertebral implant comprising:
   a first component having a first articulating surface and a first bone engagement surface for engaging a first vertebra; and
   a second component having a second articulating surface and a second bone engagement surface for engaging a second vertebra adjacent to the first vertebra, wherein the second articulating surface articulates with the first articulating surface for replicating a natural spinal movement and wherein the first and second components define an outer surface shaped as an envelope of five cylinders for contact with endplates of adjacent vertebra.

2. The intervertebral implant of claim 1, wherein the first and second articulating surfaces have equal radii of curvature in a coronal plane and different radii of curvature in a sagittal plane.

3. The intervertebral implant of claim 2, wherein the first articulating surface includes a concave portion in the coronal and sagittal plane, and the second articulating surface includes a convex portion in the coronal and sagittal plane.

4. The intervertebral implant of claim 1, wherein the first articulating surface comprises a convex portion in the coronal plane and a concave portion in the sagittal plane, and the second articulating surface includes a concave portion in the coronal plane and convex portion in the sagittal plane.

5. The intervertebral implant of claim 4, wherein in the sagittal plane the curvatures of the respective convex and concave portions of the first and second articulating surfaces are different.

6. The intervertebral implant of claim 5, wherein in the coronal plane the first articulating surface is V-shaped with a rounded tip.

7. The intervertebral implant of claim 1, further comprising bone engagement formations arranged in parallel rows on the first and second bone engagement surfaces.

8. The intervertebral implant of claim 1, wherein each cylinder has a circular cross-section.

9. The intervertebral implant of claim 1, wherein at least one of the five cylinders has a length, which is greater than a diameter of the at least one of the five cylinders.

10. A surgical device comprising:
a modular intervertebral implant having an outer surface substantially shaped as an envelope of five cylinders, the outer surface having a first bone engagement surface and a second bone engagement surface, with a first articulating surface formed opposite the first bone engagement surface and a second articulating surface formed opposite the second bone engagement surface, the first articulating surface articulating with the second articulating surface for replicating natural spine movement, each of the first bone engagement surface and second bone engagement surface arranged to be in contact in situ with endplates of adjacent vertebra.

11. The surgical device of claim 10, wherein four of the five cylinders intersect the fifth cylinder.

12. The surgical device of claim 10, wherein each cylinder has a circular cross-section.

13. The surgical device of claim 10, wherein the five cylinders include a central cylinder and first, second, third and fourth smaller corner cylinders surrounding the central cylinder.

14. The intervertebral implant of claim 10, wherein the first bone engagement surface and the second bone engagement surface are capable of being substantially received between endplates of adjacent vertebra.

15. The surgical device of claim 13, wherein the intervertebral implant includes:
a first component having the first articulating surface and the first bone engagement surface for engaging a first vertebra, the first component including the first and second corner cylinders and a first portion of the central cylinder; and
a second component separate from the first component and having the second articulating surface and the second bone engagement surface for engaging a second vertebra adjacent to the first vertebra, the second component including the third and fourth corner cylinders and a second portion of the central cylinder.

16. The surgical device of claim 15, wherein the first bone engagement surface includes outer surfaces of the first and second corner cylinders and an outer surface of the first portion of the central cylinder.

17. The surgical device of claim 16, wherein the second bone engagement surface includes outer surfaces of the third and fourth corner cylinders and an outer surface of the second portion of the central cylinder.

18. The surgical device of claim 15, wherein the first and second articulating surfaces have equal radii of curvature in a coronal plane and different radii of curvature in a sagittal plane.

19. The intervertebral implant of claim 18, wherein the first articulating surface includes a concave portion in the coronal and sagittal plane, and the second articulating surface includes a convex portion in the coronal and sagittal plane.

20. The intervertebral implant of claim 15, wherein the first articulating surface comprises a convex portion in the coronal plane and a concave portion in the sagittal plane, and the second articulating surface includes a concave portion in the coronal plane and convex portion in the sagittal plane.

21. The intervertebral implant of claim 20, wherein in the sagittal plane the curvatures of the respective convex and concave portions of the first and second articulating surfaces are different.

22. The intervertebral implant of claim 21, wherein in the coronal plane the first articulating surface is V-shaped with a rounded tip.

23. An intervertebral implant comprising:
a first component having a first articulating surface and a first bone engagement surface for engaging an endplate of a first vertebra; and
a second component having a second articulating surface and a second bone engagement surface for engaging an endplate of a second vertebra adjacent to the first vertebra, wherein the second articulating surface contacts and articulates relative to the first articulating surface for replicating a natural spinal movement, wherein the first and second articulating surfaces have equal radii of curvature in a coronal plane and different radii of curvature in a sagittal plane, and wherein the first and second bone engagement surfaces define an outer surface shaped as an envelope of five cylinders.

24. The intervertebral implant of claim 23, wherein the first articulating surface includes a concave portion in the coronal and sagittal plane, and the second articulating surface includes a convex portion in the coronal and sagittal plane.

25. The intervertebral implant of claim 24, further comprising bone engagement formations arranged in substantially parallel rows on the first and second bone engagement surfaces.

26. The intervertebral implant of claim 23, wherein the first component and the second component are positionable wholly between the endplates of the first vertebra and second vertebra.

* * * * *

UNITED STATES PATENT AND TRADEMARK OFFICE
CERTIFICATE OF CORRECTION

PATENT NO. : 8,721,722 B2
APPLICATION NO. : 11/567272
DATED : May 13, 2014
INVENTOR(S) : Gretchen Dougherty Shah et al.

It is certified that error appears in the above-identified patent and that said Letters Patent is hereby corrected as shown below:

In the Specification:

Column 4, Description Of Various Aspects, Line 53, delete "inferior and superior" and insert --superior and inferior--, therefor Column 4, Description Of Various Aspects, Line 56-57, delete "inferior and superior" and insert --superior and inferior--, therefor Column 6, Description Of Various Aspects, Line 8-9, delete "engagement formations" and insert --bone engagement formations--, therefor Column 6, Description Of Various Aspects, Line 63, delete "tip" and insert --distal tip--, therefor Column 7, Description Of Various Aspects, Line 44, delete "drill cannula" and insert --drill guide cannula--, therefor Column 7, Description Of Various Aspects, Line 53, delete "240" and insert --206--, therefor Column 8, Description Of Various Aspects, Line 20, delete "cannula" and insert --drill guide cannula--, therefor Column 10, Description Of Various Aspects, Line 57, delete "racks" and insert --serrated racks--, therefor Column 10, Description Of Various Aspects, Line 60, delete "engagement formations 312" and insert --bone engagement formations 302--, therefor Column 11, Description Of Various Aspects, Line 21, delete "diameter drills" and insert --cannulated drills--, therefor Signed and Sealed this
Twenty-first Day of October, 2014

Michelle K. Lee
*Deputy Director of the United States Patent and Trademark Office*

CERTIFICATE OF CORRECTION (continued)
U.S. Pat. No. 8,721,722 B2

In the Claims:

Column 13, Claim 14, Line 56, after "being", delete "substantially", therefor

Column 14, Claim 25, Line 56-57, after "in", delete "substantially", therefor